United States Patent
Hruska et al.

(10) Patent No.: US 6,294,320 B1
(45) Date of Patent: Sep. 25, 2001

(54) CELL MATRIX PLAQUES OF INITIAL BONE FORMATION

(75) Inventors: Keith Hruska; Magdalena Wozniak, both of St. Louis, MO (US)

(73) Assignee: Barnes-Jewish Hospital, St. Louis, MO (US)

(*) Notice: Subject to any disclaimer, the term of this patent is extended or adjusted under 35 U.S.C. 154(b) by 0 days.

(21) Appl. No.: 09/454,330

(22) Filed: Dec. 3, 1999

Related U.S. Application Data

(60) Provisional application No. 60/110,878, filed on Dec. 4, 1998.

(51) Int. Cl.$^7$ ............................... C12Q 3/00; C12N 5/06; C07K 16/00; C12P 21/08

(52) U.S. Cl. ......................... 435/4; 435/343; 435/343.1; 530/388.7

(58) Field of Search ..................................... 424/484, 425; 435/4, 69.1, 240.1, 240.2, 343; 530/317, 388.7

(56) References Cited

U.S. PATENT DOCUMENTS 5,861,306 * 1/1999 Pugh et al. .
6,007,833 * 12/1999 Chudzik et al. .

OTHER PUBLICATIONS

J.E. Folk, Transglutaminases, 1980, Ann. Rev. Biochem., vol. 49, pp. 517–531.

Martha Somerman, et al., Mechanism of Fibroblast Attachment to Bone Extracellular Matrix: Role of a 44 Kilodalton Bone Phosphoprotein, 1987, Journal of Bone and Mineral Research, vol. 2, pp. 259–265.

David A. Cheresh, et al., Biosynthetic and Functional Properties of an Arg–Gly–Asp–directed Receptor Involved in Human Melanoma Cell Attachment to Vitronectin, Fibrinogen, and von Willebrand Factor, 1987, The Journal of Biological Chemistry, vol. 262, pp. 17703–17711.

Maureen Owen, Marrow Stromal Stem Cells, 1988, J. Cell Sci. Suppl., vol. 10, pp. 63–76.

Matthew Pead, et al., Direct Transformation from Quiescence to Bone Formation in the Adult Periosteum Following a Single Brief Period of Bone Loading, 1988, Journal of Bone and Mineral Research, vol. 3, pp. 647–656.

Ake Oldberg, et al., Identification of a Bone Sialoprotein Receptor in Osteosarcoma Cells, 1988, The Journal of Biological Chemistry, vol. 263, pp. 19433–19436.

John M. Wozney, et al., Novel Regulators of Bone Formation: Molecular Clones and Activities, 1988, Science, vol. 242, pp. 1528–1534.

Martha J. Somerman, et al., Cell Attachment Activity of the 44 Kilodalton Bone Phosphoprotein is not Restricted to Bone Cells, 1989, Matrix, vol. 9, pp. 49–54.

Donald R. Senger, Purification of a Human Milk Protein Closely Similar to Tumor–Secreted Phosphoproteins and Osteopontin, 1989, Biochimica et Biophysica Acta, vol. 996, pp. 43–48.

Hannu Larjava, et al., Novel Function for $\beta_1$ Integrins in Keratinocyte Cell–Cell Interactions, 1990, The Journal of Cell Biology, vol. 110, pp. 803–815.

Takenobu Katagiri, et al., The Non–Osteogenic Mouse Pluripotent Cell Line, C3H10T1/2, is Induced to Differentiate into Osteoblastic Cells by Recombinant Human Bone Morphogenetic Protein–2, 1990, Biochemical and Biophysical Research Communications, vol. 172, pp. 295–299.

John J. Sauk, et al., Persistent Spreading of Ligament Cells on Osteopontin/Bone Sialoprotein–I or Collagen Enhances Tolerance to Heat Shock, 1990, Experimental Cell Research, vol. 188, pp. 105–110.

L.C. Gerstenfeld, et al, Expression and Ultrastructural Immunolocalization of a Major 66 kDa Phosphoprotein Synthesized by Chicken Osteoblasts During Mineralization In Vitro, 1990, The Anatomical Record, vol. 228, pp. 93–103.

Michael J. Buckley, DDS, et al., The Effects of Mechanical Strain on Osteoblasts In Vitro, 1990, J. Oral Maxillofac Surg., vol. 48, pp. 276–282.

Akira Yamaguchi, et al., Recombinant Human Bone Morphogenetic Protein–2 Stimulates Osteoblastic Maturation and Inhibits Myogenic Differentiation In Vitro, 1991, The Journal of Cell Biology, vol. 113, pp. 681–687.

Charles W. Prince, et al, Osteopontin, A Substrate for Transglutaminase and Factor XIII Activity, 1991, Biochemical and Biophysical Research Communications, vol. 177, pp. 1205–1210.

Arnold I. Caplan, Mesenchymal Stem Cells, 1991, Journal of Orthopaedic Research, vol. 9, pp. 641–650.

Akimitsu Miyauchi, et al, Recognition of Osteopontin and Related Peptides by an $\alpha_v\beta_3$ Integrin Stimulates Immediate Cell Signals in Osteoclasts, 1991, The Journal of Biological Chemistry, vol. 266, pp. 20369–20374.

Yen Chen, et al., Calcium and Collagen Binding Properties of Osteopontin, Bone Sialoprotein, and Bone Acidic Glycoprotein–75 from Bone, 1992, The Journal of Biological Chemistry, vol. 267, pp. 24871–24878.

T. Kuber Sampath, et al., Recombinant Human Osteogenic Protein–1 (hOP–1) Induces New Bone Formation in Vivo with a Specific Activity Comparable with Natural Bovine Osteogenic Protein and Stimulates Osteoblasts Proliferation and Differentiation in Vitro, 1992, The Journal of Biological Chemistry, vol. 267, pp. 20352–20362.

(List continued on next page.)

Primary Examiner—Leon B. Lankford, Jr.
Assistant Examiner—Michele C. Flood
(74) Attorney, Agent, or Firm—Senniger, Powers, Leavitt & Roedel

(57) ABSTRACT

An isolated and essentially purified cell matrix plaque of initial bone formation comprising of $\alpha_v\beta_3$ integrin and rapid assays using such cell matrix plaques to measure potentials of factors, regimens or tissues for stimulation and/or inhibition of bone formation.

17 Claims, 12 Drawing Sheets

OTHER PUBLICATIONS

Figure 1A:
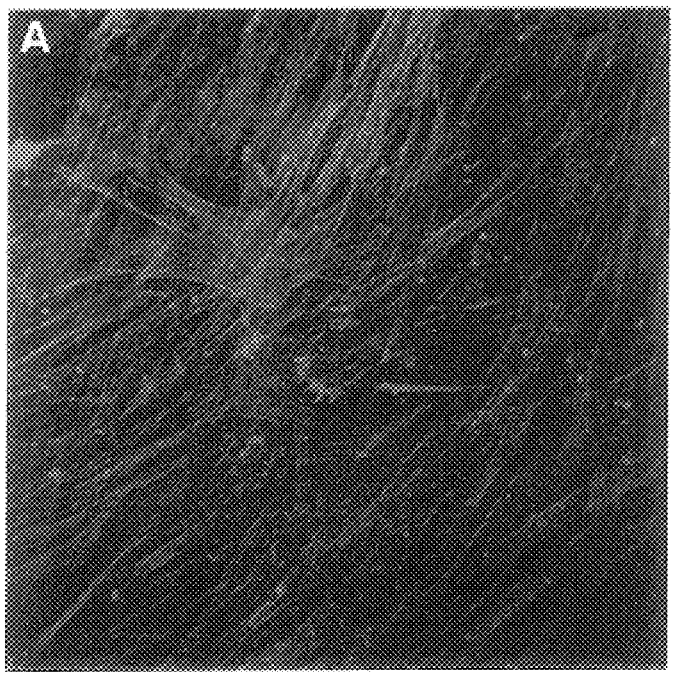

Ian Zachary/Enrique Rozengurt, Focal Adhesion Kinase (p125$^{FAK}$): A Point of Convergence in the Action of Neuropeptides, Integrens, and Oncogenes, 1992, Cell, vol. 71, pp. 891–894.

F. Patrick Ross, et al., Interactions between the Bone Matrix Proteins Osteopontin and Bone Sialoprotein and the Osteoclast Integrin $\alpha_v\beta_3$ Potentiate Bone Resorption, 1992, The Journal of Biological Chemistry, vol. 268, pp. 9901–9907.

Anne Ridley and Alan Hall, The Small GTP–Binding Proteein rho Regulates the Assembly of Focal Adhesions and Actin Stress Fibers in Response to Growth Factors, 1992, Cell, vol. 70, pp. 389–399.

Daniel Aeschlimann, et al., Expression of Tissue Transglutaminase in Skeletal Tissues Correlates with Events of Terminal Differentiation of Chondrocytes, 1993, The Journal of Cell Biology, vol. 120, pp. 1461–1470.

Graeme Hunter and Harvey Goldberg, Nucleation of Hydroxyapatite by Bone Sialoprotein, 1993, Proc. Natl. Acad. Sci., vol. 90, pp. 8562–8565.

David Denhardt and Xiaojia Guo, Osteopontin: A Protein with Diverse Functions, 1992, The FASEB Journal, vol. 7, pp. 1475–1482.

T. Kubota, et al., Influence of an Intermittent Compressive Force on Matrix Protein Expression by ROS 17/2.8 Cells, With Selective Stimulation of Osteopontin, 1993, Archs Oral Biol., vol. 38, pp. 23–30.

A. Sonnenberg, Integrins and Their Ligands, 1993, Current Topics in Microbiology and Immunology, vol. 184, pp. 7–35.

Takenobu Katagiri, et al., Bone Morphogenetic Protein–2 Converts the Differentiation Pathway of C2C12 Myoblasts into the Osteoblasts Lineage, 1994, The Journal of Cell Biology, vol. 127, pp. 1755–1766.

Su–Li Cheng, et al., Differentiation of Human Bone Marrow Osteogenic Stromal Cells In Vitro: Induction of the Osteoblast Phenotype by Dexamethasone, 1994, Endocrinology, vol. 134, pp. 277–286.

Daniel Aeschlimann, Mats Paulsson, Tranglutaminases: Protein Cross–Linking Enzymes in Tissues and Body Fluids, 1994, Thrombosis and Haemostasis, vol. 71, pp. 402–415.

Esben S. Sorensen, et al., Localization of Transglutaminase—Reactive Glutamine Residues in Bovine Osteopontin, 1994, Biochem. J., vol. 304, pp. 13–16.

W. Grzesik and P. Robey, Bone Matrix RGD Glycoproteins: Immunolocalization and Interaction with Human Primary Osteoblastic Bone Cells in Vitro, 1994, Journal of Bone and Mineral Research, vol. 9, pp. 487–496.

J.A. Gilbert, et al., Strain Profiles for Circular Cell Culture Plates Containing Flexible Surfaces Employed to Mechanically Deform Cells In Vitro, 1994, J. Biomechanics, vol. 27, pp. 1169–1177.

Simone Beninati, et al., Osteopontin: Its Transglutaminase-Catalyzed Posttranslational Modifications and Cross–Linking to Fibronectin, 1994, J. Biochem., vol. 115, pp. 675–682.

Daniel Aeschlimann, et al., Transglutaminase–catalyzed Matrix Cross–Linking in Differentiation Cartilage: Identification of Osteonectin as a Major Glutaminyl Substrate, 1995, The Journal of Cell Biology, vol. 129, pp. 881–892.

Keith A. Hruska, et al., Engagement of the Osteoclast Integrin $\alpha_v\beta_3$ by Osteopontin Stimulates Phosphatidylinositol 3–Hydroxyl Kinase Activity, 1995, Endocrinology, vol. 136, pp. 2984–2991.

L. V. Harter, et al., Human Osteoblast–Like Cells Respond to Mechanical Strain with Increased Bone Matrix Protein Production Independent of Hormonal Regulation, 1995, Endocrinology, vol. 136, pp. 528–535.

Martin A. Schwartz, et al., Integrins: Emerging Paradigms of Signal Transduction, 1995, Annu. Rev. Cell Dev. Biol., vol. 11, pp. 549–599.

Neil Hotchin and Alan Hall, The Assembly of Integrin Adhesion Complexes Requires Both Extracellular Matrix and Intracellular rho/rac GTPases, 1995, The Journal of Cell Biology, vol. 131, pp. 1857–1865.

Clark M. Stanford, et al., Rapidly Forming Apatitic Mineral in an Osteoblastic Cell Line (UMR 106_01 BSP), 1995, JBC, vol. 270, pp. 9420–9428.

Susan Craig and Robert Johnston, Assembly of Focal Adhesions: progress, paradigms, and portents, 1996, Current Opinion in Cell Biology, vol. 8, pp. 74–85.

M. Chellaiah, et al., Osteopontin Activation of c–src in Human Melanoma Cells Requires the Cytoplasmic Domain of the Integrin $\alpha_v$–Subunit, 1996, Endocrinology, vol. 137, pp. 2432–2440.

Susan LaFlamme and Kelly Auer, Integrin Signaling, 1996, Cancer Biology, vol. 7, pp. 111–118.

Paloma Sanchez–Mateos, et al., Regulation of Integrin Function, 1996, Cancer Biology, vol. 7, pp. 99–109.

Carl T. Brighton, M.D., Ph.D., et al., The Biochemical Pathway Mediating the Proliferative Response of Bone Cells to a Mechanical Stimulus, 1996, The Journal of Bone and Joint Surgery, vol. 78–A, pp. 1337–1347.

Meenakshi Chellaiah and Keith Hruska, Osteopontin Stimulates Gelsolin–Associated Phosphoinositide Levels and Phosphatidylinositol Triphosphate–Hydroxyl Kinase, 1996, Molecular Biology of the Cell, vol. 7, pp. 743–753.

Magdalena Wozniak and Lee Limbird, The Three $\alpha_2$Adrenergic Receptor Subtypes Achieve Basolateral Localization in Madin–Darby Canine Kidney II Cells via Different Targeting Mechanisms, 1996, The Journal of Biological Chemistry, vol. 271, pp. 5017–5024.

C.D. Toma, et al., Signal Transduction of Mechanical Stimuli Is Dependent on Microfilament Integrity: Identification of Osteopontin as a Mechanically Induced Gene in Osteoblasts, 1997, Journal of Bone and Mineral Research, vol. 12, pp. 1626–1636.

Fernando Lecanda, et al., Regulation of Bone Matrix Protein Expression and Induction of Differentiation of Human Osteoblasts and Human Bone Marrow Stromal Cells by Bone Morphogenetic Protein–2, 1997, Journal of Cellular Biochemistry, vol. 67, pp. 386–398.

D.E. Ingber, Tensegrity: The Architectural Basis of Cellular Mechanotransduction, 1997, Annu. Rev. Physiol. vol. 59, pp. 575–579.

R.A. Jones, et al., Reduced expression of tissue transglutaminase in a human endothelial cell line leads to changes in cell spreading, cell adhesion and reduced polymerisation of fibronectin, 1997, Journal of Cell Science, vol. 110, pp. 2461–2472.

D.M. Slater, et al., Electrophysiological Responses of Human Bone Cells to Mechanical Stimulation: Evidence for Specific Integrin Function in Mechanotransduction, 1997, Journal of Bone and Mineral Research, vol. 12, pp. 1133–1141.

Keigo Hanada, et al., Stimulatory Effects of Basic Fibroblast Growth Factor and Bone Morphogenetic Protein–2 on Osteogenic Differentiation of Rat Bone Marrow–Derived Mesenchymal Stem Cells, 1997, Journal of Bone and Mineral Research, vol. 12, pp. 1606–1614.

T.A. Einhorn, One of Nature's Best Kept Secrets, 1998, Journal of Bone and Mineral Research, vol. 13, pp. 10–12.

Jane Aubin, Arnold Kahn, The Osteoblast Lineage–Embryologic Origins and the Differentiation Sequence.

Zohar et al. Journal of Cellular Physiology, 70: 88–100. Single cell analysis of intracellular osteopontin in osteogenic cultures of fetal rat calvarial cells, 1997.*

Malaval et al. Journal of Cellular Physiology, 158 (3), pp 555–72. Cellular expression of bone–related proteins during in vitro osteogenesis in rat bone marrow stromal cells, Mar. 1994.*

Cheifetz et al. Connective Tissue Research, 35, pp 1–4 and 71–78. Influence of osteogenic protein–1 (OP–1; BMP–7) and transforming growth factor–beta 1 on bone formation in vitro, 1996.*

Hruska et al. Endocrinology, 136 (7), pp 2984–92. Engagement of the osteoclast integrin alpha sub v beta sub three by osteopontin stimulates phosphatidylinositol 3–hydroxyl kinase activity, Jul. 1995.*

Gupta et al. Bone 18 (2), pp 87–95. Cellular distribution and regulation of NHE–1 isoform of the Na—H exchangetr in the avian osteoclast, 1997.*

* cited by examiner

FIG. IC
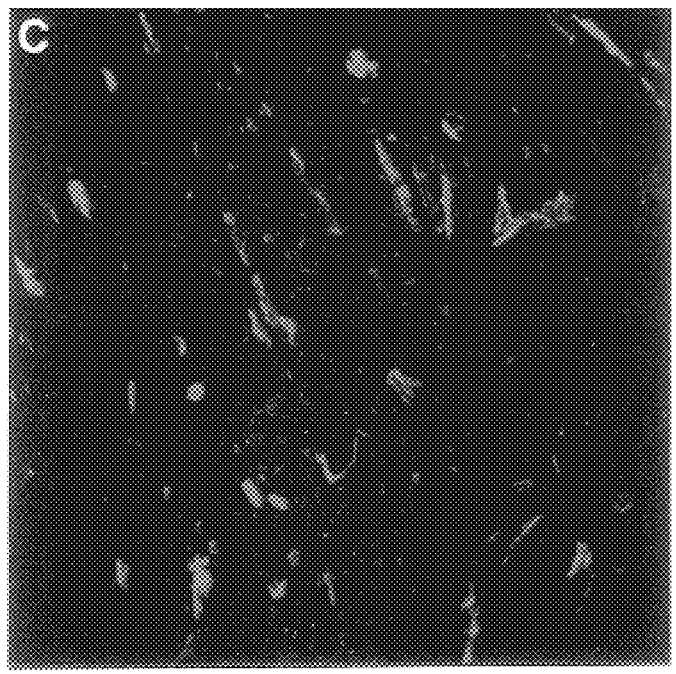
FIG. ID
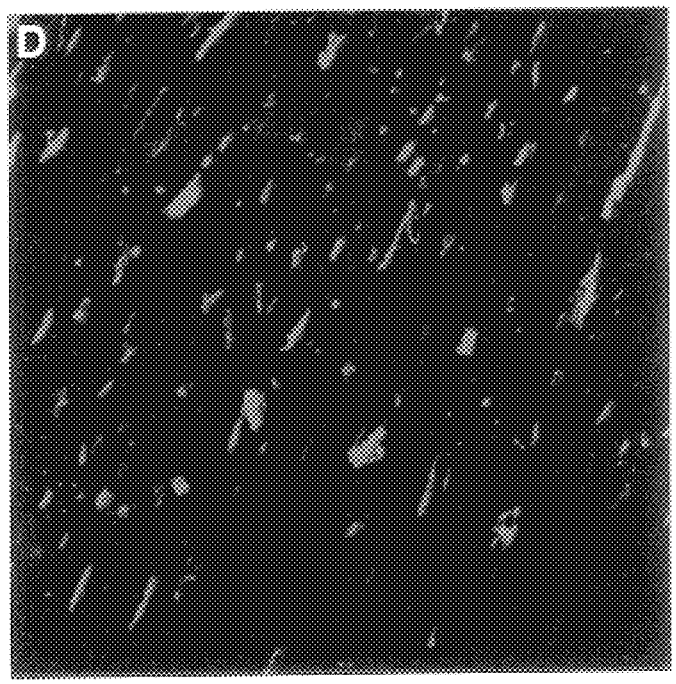

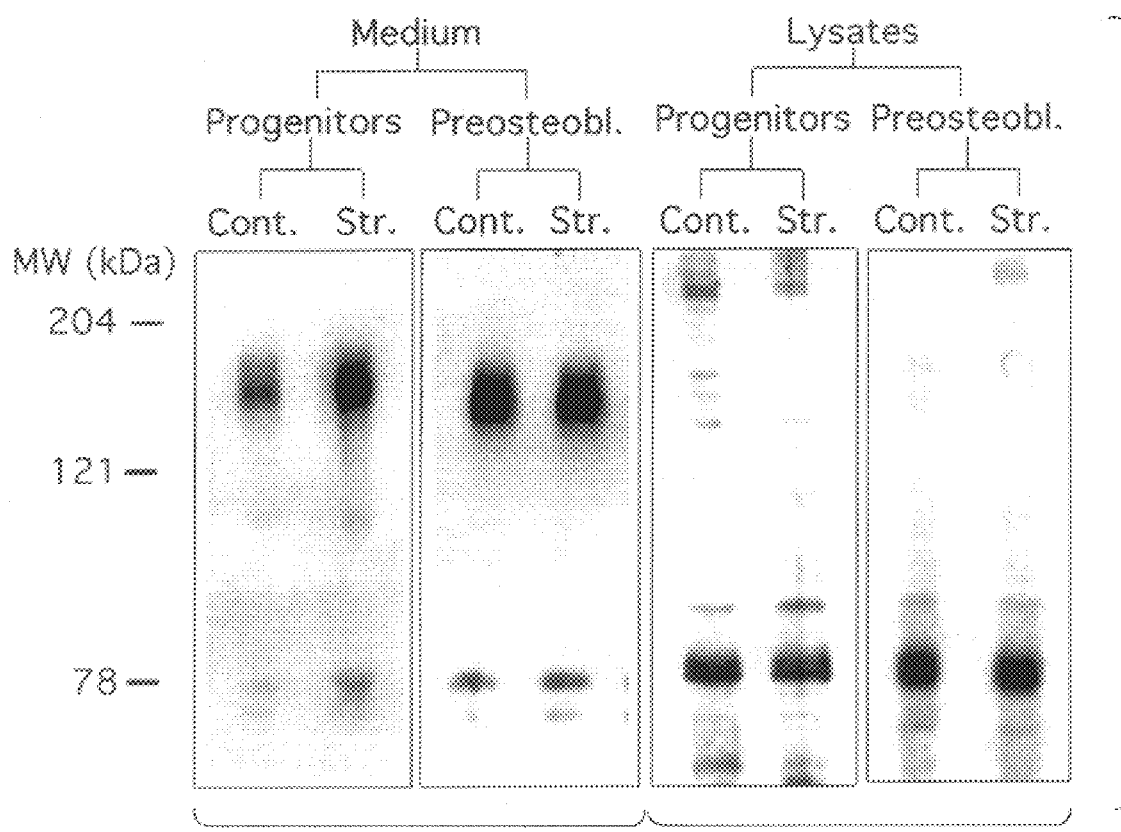

CELL MATRIX PLAQUES OF INITIAL BONE FORMATION

The contents of Applicant's provisional application Ser. No. 60/110,878 filed Dec. 4, 1998 are hereby incorporated by reference.

This invention was made with Government support under National Institute of Health grant nos. AR39561 and AR32087. The Government has certain rights in the invention.

BACKGROUND OF THE INVENTION

This invention relates to cell matrix plaques of initial bone formation and to rapid in vitro assays using such newly discovered cell matrix plaques to measure potentials of factors or tissues for stimulating and/or inhibiting bone formation. In particular, the invention relates to assays utilizing the process of $\alpha_v\beta_3$ expression, matrix protein secretion into the plaques and mineralization of such plaques developed using primary cultures from the human osteoblast lineage.

Bone cells are known to transduce mechanical signals from the environment into anabolic biochemical responses through the process of mechanotransduction. However, the precise mechanisms of mechanotransduction have been a mystery.

Osteoblasts are the skeletal cells that produce and regulate the deposition and mineralization of calcified bone matrix under the influence of the bone morphogenetic proteins (1–4).

Osteoblasts derive from osteoprogenitors, which in turn arise from multipotential mesenchymal cells (5,6). Osteoprogenitors exist in an uncommitted stage which may differentiate into one of several cell lineages, including osteoblasts, chondrocytes, fibroblasts, myocytes and adipocytes, depending on growth conditions (7–9).

The progression from early progenitors to fully functional osteoblasts that synthesize and mineralize matrix is gradual (10).

Differentiation leads through the preosteoblast stage, defined as cells expressing osteoblastic characteristics but not yet mineralizing the extracellular matrix.

The cells in the osteoblast program can be identified based on distinct morphological features and histochemical markers.

Mechanical strain is known to have potent anabolic effects on the skeleton and bone homeostasis in vivo (11), and well documented proliferative effects both in vivo and in vitro (12,13).

The tensegrity model of mechanotransduction (14) proposes that mechanical signals are integrated and converted to biochemical responses through changes in cellular architecture.

Transmembrane molecules (integrins) connecting extracellular and cytoskeletal structures may play key roles in tensegrity, however, the precise processes and molecules that transduce mechanical stimuli into cellular responses, including proliferation are not known.

Integrins are a diverse family of heterodimeric cell surface receptors which connect the cytoskeleton to the extracellular matrix and mediate a variety of signaling cascades.

The rationale for adapting the tensegrity hypothesis to the response of the cells in the osteoblast lineage to mechanical strain derived from the findings that repetitive strain of human osteoblast-like cells stimulated cell proliferation, transcription of bone matrix proteins and production of bone matrix (15–17).

The communication between osteoblasts and extracellular matrix proteins is believed to rely on integrins that are known to serve as receptors for matrix proteins.

Even though the precise role of integrins in human bone formation is just beginning to unravel, a number of cellular processes including proliferation are thought to result from the interactions between integrins present on bone cell surface and extracellular matrix proteins.

Human osteoblasts are known to express numerous a and P integrin subunits (18,19), each component having large extracellular domains responsible for ligand binding, a transmembrane domain and a short cytoplasmic domain responsible for interacting with the actin cytoskeleton (20, 21).

Integrins are known to associate with signaling molecules in focal adhesions.

Focal adhesions are defined as cell-matrix adhesion structures which contain talin, vinculin and other proteins required for integrin attachment to actin filaments, and have been described in numerous cell types but not osteoblasts.

Focal adhesions play dual roles as cell signaling structures as well as architectural links between the cellular cytoskeleton and the extracellular matrix proteins (22).

One of the extracellular matrix proteins of bone, osteopontin, is a non-collagenous glycoprotein that binds to cell surface integrins via the adhesive arginine-glycine-aspartate (RGD) motif (23–25).

Osteoblasts express high levels of osteopontin during bone matrix maturation and mineralization, where it is known to modulate (either inhibit or stimulate) the mineralization of bone matrix (16).

In addition, osteopontin promotes cellular adherence of osteoblast-like cells (26–29) and was shown to specifically interact with the $\alpha_v\beta_3$ integrin (25,26,30).

A precise method for measuring new bone formation, particularly at the subcellular level, has long eluded those interested in bone disease, repair and regeneration. The absence of such a definitive method makes it difficult to evaluate target compositions or regimens for their ability to stimulate or inhibit bone formation or extracellular matrix mineralization. Prior art methods generally suffer from inaccuracy, require making gross determinations from whole cultures, and are typically both time and labor intensive.

SUMMARY OF THE INVENTION

Among the objects of the invention, therefore, may be noted the provision of isolated and essentially purified plaques of initial bone formation and methods of assaying utilizing such plaques. Such assays may be used to screen substances or regimens which stimulate or inhibit bone formation or matrix mineralization. Since the assays operate at the subcellular level, only minute amounts of tissue are required to conduct the assay. Further, the assays may be conducted repeatedly using a single bone donor. The assays can be conducted rapidly and are not labor intensive.

Briefly, therefore, the present invention is directed to a method of measuring new bone formation using a rapid in vitro assay.

The method involves:
1. extracting bone marrow stromal cells from bone marrow cavities and growing them to semi-confluence;
2. exposing the cells to a candidate medium or regimen for osteogenesis or inhibition of osteogenesis;

3. determining the mineralization/development of bone plaque; and,
4. optionally, comparing the mineralization/development of bone plaque generated using the candidate medium or regimen with the mineralization/development of bone plaque using a preselected control such as bone morphogentic factor-7 (BMP-7), also known as osteogenic factor-I(OP-1).

Alternatively, the assay can be used as a diagnostic screen for healthy and/or deficient bone formation, making the variable the cells being observed for production of mineralization/bone plaque formation.

Other objects and features will be in part apparent and in part pointed out hereinafter.

BRIEF DESCRIPTION OF DRAWINGS AND ABBREVIATIONS

The following abbreviations used herein have the following meanings:

RGD-arginine-glycine-aspartate, BMP-bone morphogenetic protein, BSA-bovine serum albumin, Cy2-Cy2 cyanine, Cy3-indocarbocyanine, FAK-focal adhesion kinase, FCS-fetal calf serum, FITC-fluorescin isothiocyanate, OP-1-osteogenic protein-1, Figure legends:

FIG. 1 depicts localization of the $\alpha_v\beta_3$ integrin in human osteoprogenitor cells. The $\alpha_v\beta_3$ integrin was detected by immunostaining in the presence (images A and B) or in the absence (images C and D) of Triton TX-100 in the fixation protocol of cells mechanically strained for 48 hours (images B and D) and in control cells (images A and C). Cells were incubated with a mouse monoclonal antibody directed against anti-human $\alpha_v\beta_3$ integrin, followed by7 an incubation with a secondary Cy-3 conjugated anti-mouse antibody, as described in Methods. The presented images were generated using Zeiss confocal microscope and are representative of greater than 15 experiments with similar results. The magnification of the optical system used was 630.

FIG. 2 depicts localization of the $\alpha_v\beta_3$ integrin in human preosteoblasts. The $\alpha_v\beta_3$ integrin was immunolocalized in ostcoprogenitor cells incubated in OP-1 (BMP-7)-containing osteogenic medium for 48 hours in the presence (images A and B) or in the absence (images C and D) of Triton TX-100 cells mechanically strained for 48 hours (images B and D ) and in control cells (images A and C). Cells were incubated with a mouse monoclonal antibody directed against anti-human $\alpha_v\beta_3$ integrin, followed by an incubation with a secondary Cy-3 conjugated anti-mouse antibody, as described in Methods. The presented images are generated using a Zeiss confocal microscope and are representative of greater than 6 experiments with similar results. The magnification of the optical system used was 630.

FIG. 3 depicts colocalization of the $\alpha_v\beta_3$ integrin with Focal Adhesion Kinase in human preosteoblasts. The $\alpha_v\beta_3$ integrin shown in image B was colocalized (as presented in image C) with Focal Adhesion Kinase (image A) in the absence of Triton TX-100 in preosteoblasts incubated in OP-1 (BMP-7)-containing ostcogenic medium and mechanically strained for 48 hours. Arrows indicated a few of the sites where the expression of FAK was confined to the boundaries of the $\alpha_v\beta_3$ integrin plaques. Cells are incubated with a combination of a mouse monoclonal antibody directed against anti-human $\alpha_v\beta_3$ integrin and a rabbit polyclonal antibody against FAK, followed by an incubation with a mix of two secondary antibodies: Cy-2 conjugated anti-mouse and Cy-3 conjugated anti-rabbit antibody, as described in Methods. The presented images were generated using a Zeiss confocal microscope and are representative of greater than 10 experiments with similar results. Colocalization of $\alpha_v\beta_3$ integrin with FAK in the plaques following strain was observed in osteoprogenitors similar to the preosteoblasts shown in this figure. The magnification of the optical system used was 630.

Figure 4:
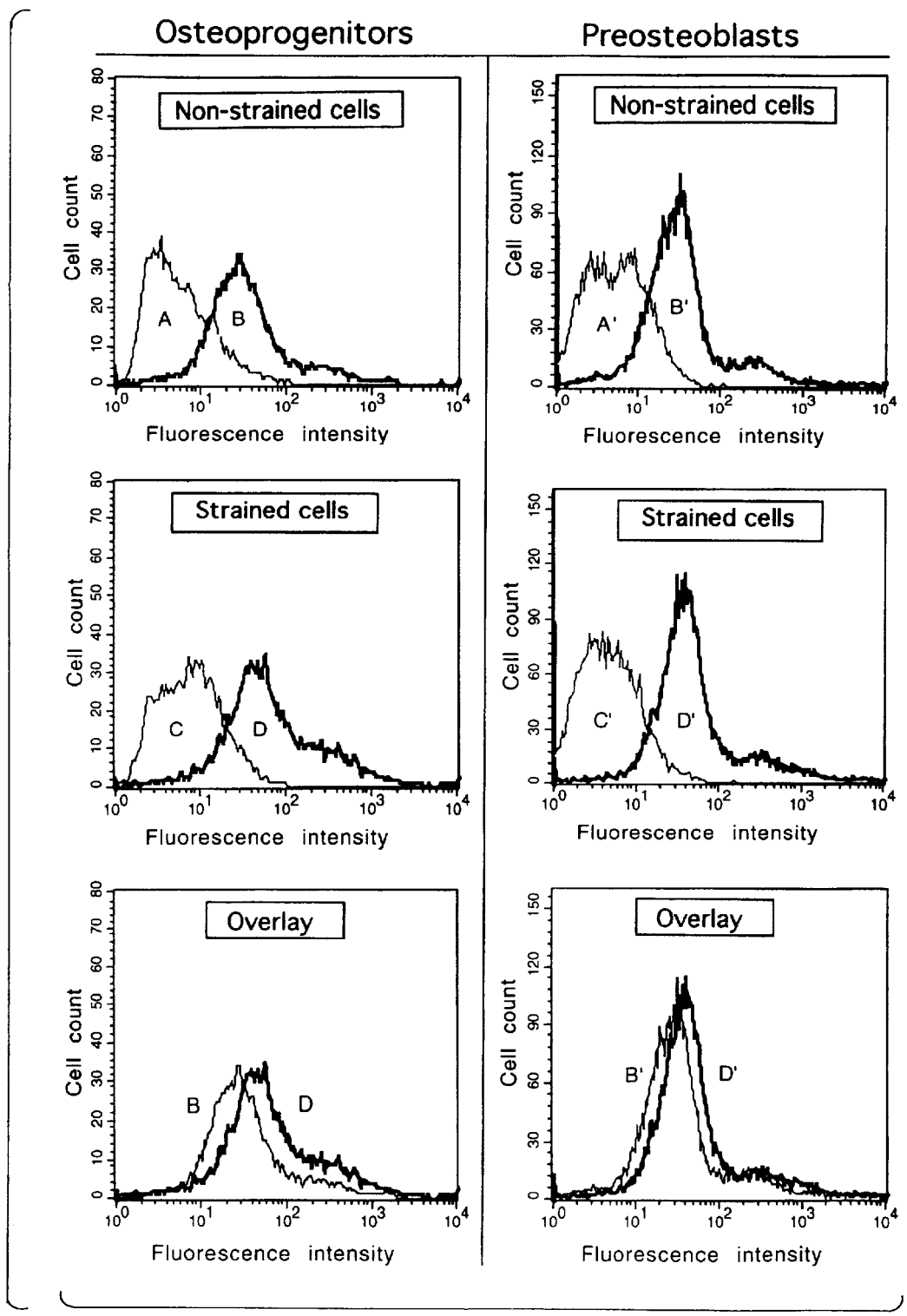

FIG. 4 is a graphic representation of flow cytometric analysis of the expression of the $\alpha_v\beta_3$ integrin on the cell surface of human osteoprogenitors and preosteoblasts. The imunofluorescence intensity due to the cell surface expression of the $\alpha_v\beta_3$ integrin was examined in single cell suspensions of cells mechanically strained for 48 hours as well as in their non-strained controls. Osteoprogenitors (left-side panels) and preosteoblasts (right-side panels) were incubated with a mouse monoclonal antibody directed against anti-human $\alpha_v\beta_3$ integrin, followed by an incubation with a secondary FITC-conjugated anti-mouse antibody, as described in Methods. The presented histograms showing the fluorescence intensity (X axes) plotted against the relative cell number (Y axes) reflect the results of at least 3 experiments done in each cell culture type. The A, A', C and C' plots represent the fluorescence detected with a negative control mouse IgG. The B, B', D and D' plots who the fluorescence level observed in cells incubated with the anti-$\alpha_v\beta_3$ integrin antibody. A, B, A' and B' show the results of flow cytometric analysis in non-strained control cells, while C, D, C' and D' show the fluorescence level in strained cells. Each histogram is based on 10,000 events. The fluorescence levels shown in plots D (strained progenitors) and D' (strained preosteoblasts) were significantly greater than those in B (non-strained progenitors and B'(non-strained preosteoblasts) were significantly greater than those in B (non-strained progenitors) and B' (non-strained preosteoblasts), respectively at $p \leq 0.01$.

FIG. 5 depicts colocalization of the $\alpha_v\beta_3$ integrin with osteopontin in non-permeabilized human osteoprogenitors. The $\alpha_v\beta_3$ integrin (shown in green; image B) was colocalized (image C) with osteopontin (shown in red; image A) in the absence of Triton TX-100 in cells mechanically strained for 48 hours. Cells were incubated with a combination of a mouse monoclonal antibody directed against anti-human $\alpha_v\beta_3$ integrin and a rabbit polyclonal antibody against human osteopontin, followed by an incubation with a mix of two secondary antibodies: Cy-2 conjugated anti-mouse and Cy-3 conjugated anti-rabbit antibody, as described in Methods. The presented images were generated using a Zeiss fluorescent microscope and are representative of at least 15 experiments. The magnification was 630.

FIG. 6 depicts analysis of the effects of mechanical strain on osteopontin secretion in human progenitors and preosteoblasts. Osteopontin levels were analyzed in the lysates (FIG. 6b) as well as in the concentrated cell culture medium (FIG. 6a) from the progenitor and preosteoblast cultures following mechanical strain for 48 hours (Str.), as well as in non-strained control cultures (Cont.). Following gel electrophoresis of equal amounts of cell culture medium protein in each well, and protein transfer onto Immobilon-P membrane, the protein blot was incubated with a rabbit polyclonal antibody against human osteopontin, followed by an incubation with a protein A—conjugated HRP, as described in Methods. Mechanical strain increased secretion of the immunoreactivc protein band of highest intensity detected at approximately 168 kDa into cell culture medium. The densitometry rations of the 168 kDa band intensity in strained versus control cultures were 2.2±0.3 in progenitors and 0.92±0.06 in preosteoblasts (FIG. 6a). The strain over control stimulation index determined by scanning densitometry of the 78 kDa bands was approximately 1.0 for cell lysates (FIG. 6b). The presented data and densitometry ration values (mean±SE) are representative of 5 experiments to analyze osteopontin secretion into culture medium (FIG. 6a) and 3 experiments to examine osteopontin levels in cell lysates (FIG. 6b).

FIG. 7 depicts colocalization of tissue transglutaminase with the $\alpha_v\beta_3$ integrin in human osteoprogenitors. We examined the distribution of tissue transglutaminase in Triton TX-100-permeabilized cells (image A) and as well as in non-permeabilized cells (image B). Our attention was focused on the relatively large plaques of tissue transglutaminase that were visualized on the cell surface under non-permeabilizing conditions (image B). The co-immunostraining under such conditions of cell surface tissue transflutaminase (shown in image C) and the $\alpha_v\beta_3$ integrin (shown in image D) demonstrated the colocalization of the two molecules (image E) in cells mechanically strained for 48 hours. Images C-E were obtained from bone cells that were incubated with a combination of a rabbit antibody directed against tissue transglutaminase and a mouse monoclonal antibody against human $\alpha_v\beta_3$ integrin, followed by an incubation with a mix of two secondary antibodies: Cy-3 conjugated anti-rabbit and Cy-2 conjugated anti-mouse antibody, as described in Methods. The presented images were generated using a Zeiss fluorescent microscope and are representative of at least 5 experiments. The magnification was 630.

FIG. 8 depicts the effect of mechanical strain on the formation of mineralization nodules. Human bone marrow stromal cells were maintained in $\alpha$-MEM supplemented with 10% FCS in culture until confluent. Cells were then exposed to osteogenic medium containing $\alpha$-MEM supplemented with 10% FCS, 10 mM of $\beta$-glycerophosphate, 50 $\mu$g/ml of ascorbic acid and 40 ng/ml of osteogenic protein OP-1 for 18 days, mechanically strained for 48 hours (days 18–20) and then both strained cells (shown in FIGS. 8B, 8D and 8F) and their non-strained controls (shown in FIGS. 8A, 8C and 8E) were examined for the formation of mineralized nodules by alizarin red-S staining. Cells were fixed in 70% ice-cold ethanol for 1 hour and strained with 0.5% (w/v) alizarin red-S for 10 minutes, as described in Methods. Each pair of images (A–B, C–D and E–F) represent an independent experiment. The data is representative of at least 10 experiments. FIG. 8G shows colocalization (yellow) of mineralized nodules (as visualized by 1 $\mu$M calcein) and the $\alpha_v\beta_3$ integrin in cells mechanically strained for 48 hours. Cells are incubated with a combination of a mouse monoclonal antibody against human $\alpha_v\beta_3$ integrin and calcein, followed by an incubation with a secondary Cy-3 conjugated anti-mouse antibody, as described in Methods. The presented images were generated using a Zeiss fluorescent microscope and are representative of at least 5 experiments.

FIG. 9 depicts osteoblastic focal adhesions which do not contain the $\alpha_v\beta_5$ or the $\alpha_v\beta_6$ integrin. The $\alpha_v$ integrin subunit was immunodetected in focal adhesions of mechanically strained osteoprogenitors (image A) using a mouse monoclonal antibody directed against human $\alpha_v$ integrin subunit, followed by an incubation with a secondary Cy-3 conjugated anti-mouse antibody, as described in Methods. The presented $\alpha_v$ integrin image was generated using a Zeiss confocal microscope. In order to determine the identity of the $\alpha_v$ integrin in focal adhesions, the localization of the $\beta_5$ and $\beta_6$ integrin subunits, as shown in images B and D, respectively, was examined with primary rabbit polyclonal antibodies directed against these integrin subunits followed by a secondary Cy-3 conjugated anti-rabbit antibody. Image C shows the colocalization of the $\beta_5$ integrin subunit (stained with a secondary Cy-3 conjugated antibody) with the $\alpha_v\beta_3$ integrin (stained with a secondary Cy-2 conjugated antibody), as described in Methods. Arrows indicate long cellular processes and arrowheads point to sites where cellular processes abut other cell bodies at their end. The presented images were generated using a Zeiss fluorescent microscope and are representative of at least 3 experiments. The magnification of the optical system was 630.

Figure 10A:
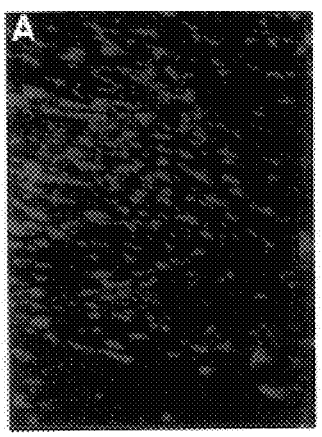

FIG. 10 depicts identification of the $\alpha_v$ integrin present in focal adhesions. The $\alpha_v$ integrin subunit (shown in image A) was colocalized (image C) with the $\beta_1$ integrin subunit (shown in image B) in cells mechanically strained for 48 hours. Cells were incubated with a combination of a mouse monoclonal antibody directed against anti-human $\alpha_v$ integrin subunit and a rabbit polyclonal antibody against human $\beta_1$ integrin subunit, followed by an incubation with a mix of two secondary antibodies: Cy-2 conjugated anti-mouse and Cy-3 conjugated anti-rabbit antibody, as described in Methods. The presented images were generated using a Zeiss fluorescent microscope and arc representative of at least 8 experiments. The magnification was 630.

DESCRIPTION OF THE PREFERRED EMBODIMENT

The contents of each of the references cited herein are incorporated by reference.

In accordance with the present invention it has been discovered that primary bone cells adhering to vitronectin and Type I collagen, demonstrate a unique form of cell-matrix interaction and a major upregulation of the $\alpha_v\beta_3$ integrin following mechanical strain. The $\alpha_v\beta_3$ integrin localized to plaque-like sites of cell/substratum interaction along with osteopontin which was expressed as a macromoieculc, possibly cross-linked by tissue transglutaminase which was also localized to the plaques. Such bone plaque sites, not previously isolated or essentially purified, are herein shown to be key indicators of bone formation and mineralization at the sub-cellular level. Such an indicator can be used, as described in detail below, to evaluate a candidate medium, or regimen (for example, employing an environmental stimulus such as mechanical strain alone or in combination with other factors) for its physiological or therapeutic potential as a stimulator or inhibitor of osteogenesis.

In general, bone cells transduce responses through the process of mechanotransduction. However, the mechanisms of mechanotransduction have been essentially unknown. To address this issue, applicants perfoined studies in primary human bone cells at three defined stages of differentiation: the osteoblasts, preosteoblasts and osteoprogenitors grown on collagen/vitronectin coated supports. Applicants discovered that a mechanical strain regimen of 70,000 $\mu$E at 0.05 Hz stimulated the expression of the $\alpha_v\beta_3$ integrin in irregular plaque-like areas of integrin-extracellular matrix protein interaction. The plaque-like areas were distinct from another type of cell matrix interaction expressed in ostcoblastic cells represented by fine and regularly spaced focal adhesions (FA) that expressed $\alpha_v$ and $\beta_1$ integrins and colocalized with vinculin and other FA markers. The unique sites of cell-matrix interaction containing $\alpha_v\beta_3$ colocalized with focal adhesion kinase but not with other FA markers. Mechanical strain increased the number and size of the plaques defined by surface expression of $\alpha_v\beta_3$ Strain also increased secretion of matrix proteins into the plaque-like areas colocalizing with the $\alpha_v\beta_3$ integrin there. Osteopontin was secreted as a cross-linked macromolecular complex, likely through the action of tissue transglutaminase which was also found in the plaques of the $\alpha_v\beta_3$ integrin-cell matrix interaction. In addition, mechanical strain increased mineralization of the extracellular matrix by osteoblasts. Since the plaque-like areas of cell-matrix organization exhibit macromolecular assembly and mineralization, they represent subcellular indicators of bone formation, and $\alpha_v\beta_3$ integrin activation represents one mechanism by which mechanical strain stimulates bone formation.

Utilizing this discovery, a method of measuring new bone formation using a rapid in vitro assay has been developed. The method involves extracting bone marrow stromal cells from bone marrow cavities and growing them to semi-confluence; exposing the cells to a candidate medium or regimen for osteogenesis or inhibition of osteogenesis; determining the mineralization/development of bone plaque; and, optionally, comparing the mineralization/development of bone plaque generated using the candidate medium or regimen with the mineralization/development of bone plaque using a preselected control such as bone morphogenetic factor-7 (BMP-7), also known as osteogenic factor-1 (OP-1).

Alternatively, the assay can be used as a diagnostic screen for healthy and/or deficient bone formation, making the variable the cells being observed for production of mineralization/bone plaque formation.

Using the techniques detailed below, a rapid, relatively high throughput screen for large-scale evaluation of bone formation has been devised. For example, using techniques known in the art, immunocytochemical/fluorescent-activated cell sorting can be employed, in which the area of plaque growth is examined under the microscope, photographed and digitized for precise measurements. Examples of such techniques for assaying for the presence of the bone plaques isolated by applicants are detailed below.

The following examples illustrate the invention, but are not to be taken as limiting the various aspects of the invention as illustrated.

EXAMPLES

Materials

The anti-$\alpha_v\beta_3$ integrin and anti-osteopontin antibodies were kindly provided by Dr. David Griggs (Monsanto). The anti-$\alpha_v\beta_3$ integrin complex monoclonal antibody (P112) behaves almost identically to the LM609 antibody (31), it appears to bind the same epitope and operate through the same mechanism of action (personal communication)[1]. The anti-$\alpha_v$ integrin subunit (L230) and anti-$\beta_6$ integrin subunit (A10) antibodies were generous gifts from Drs. Scott Blystone and Eric Brown (Washington University) and Drs. Dean Sheppard and John Chen (UCSF), respectively. The anti-tissue transglutaminase antibody was a kind gift from Dr. Daniel Aeschlimann (University of Wisconsin). The anti-$\beta_1$, -$\beta_5$ and -$\alpha_2$ integrin antibodies were obtained from Chemicon International Inc. The anti-FAK (pp125$^{FAK}$) antibody, anti-Goat Cy3-conjugated IgG and fetal calf serum were purchased from Sigma. The Cy3- and Cy2-conjugated AffiniPure Goat Anti-Mouse and Anti-Rabbit IgG were from Jackson Immunochemicals. The protein A-Horscradish Peroxidase conjugate was obtained from Transduction Research. Complete™ protease inhibitor cocktail was purchased from Boehringer Mannheim. Flex I and Flex II cell culture dishes were obtained from Flexcell Corporation. The Omeacell™ 10 ml disposable membrane cells were from Pall Filtron. Immobilon Transfer Membrane for Western blotting applications was purchased from Millipore. Ponceau S solution was obtained from Sigma. All other chemicals utilized were reagent grade.

Cell Cultures

The primary human bone marrow stromal cell cultures were prepared as described previously. Briefly, bone marrow stromal cells were collected from bone marrow cavities, treated with 1 $\mu$g/ml DNase and 10 units/ml heparin in DME/F-12 medium, then pclleted, resuspended in $\alpha$-MEM supplemented with 10% heat-inactivated FCS and separated by Ficoll/Hypaque density gradient. The interphase obtained by centrifugation was collected and resuspended in $\alpha$-MEM supplemented with 10% heat-inactivated FCS, then grown to confluency. At that time, bone marrow stromal cells were plated on collagen Type I-coated Flex I and Flex II cell culture dishes at a density of 40,000 cells/well and maintained in culture for 7–14 days, changing medium every 3–4 days. These cell cultures are

[1] Personal communication with Dr. Jeffrey W. Smith at Program on Cell Adhesion and Extracellular Matrix. The Burnham Institute 10901 North TolTey Pines Road, La Jolla, Calif. 92037. referred to as osteoprogenitors (3). These osteoprogenitor cell cultures are characterized by low, but detectable, alkaline phosphatase activity of 400 nmole pNPP/min./$\mu$g protein; osteopontin expression; absence of osteocalcin expression; and mineralization of the extracellular matrix after 20 days of culture in osteogenic media.

Bone marrow stromal cells grown to semi-confluence and then exposed to osteogenic medium containing 10 mM of $\beta$-glycerophosphate, 50 $\mu$g/ml ascorbic acid and 40 ng/ml of osteogenic protein OP-1(32) also referred to as bone morphogenetic protein-7 (BMP-7), for 48 hours were defined as preosteoblasts. These prcosteoblast cultures are characterized by alkaline phosphatase activity of 80,000 nmole pNPP/min./$\mu$g protein, osteopontin expression, absence of osteocalcin expression, and mineralization after 14 days in osteogenic media. For the purposes of this paper, bone marrow stromal cells exposed to OP-1-containing osteogenic medium for 14 days were defined as "mineralizing preosteoblasts" or osteoblasts. The osteoblast cultures are characterized by alkaline phosphatase activity of 60,000 nmole pNPP/min./$\mu$g protein, osteopontin expression, osteocalcin expression and mineralization of the extracellular matrix.

Near-confluent human preosteoblasts, osteoprogenitors, and osteoblasts were placed on Flexcell Strain Apparatus that vacuum-stretches the flexible silicone bottoms of Flex culture dishes. Applicants applied cyclic strain at three cycles/minute (10 seconds on/10 seconds off; frequency of 0.05 Hz) for 48 hours. One characteristic of the Flexcell Strain Apparatus is the nonuniformity of the strain applied across the surface of the cell culture well. The magnitude of strain delivered in these experiments ranged from approximately 120,000 microstrain ($\mu$E) at the edge of the plate (12% maximal displacement) to 0 $\mu$E at the center of each cell culture well. Strain applied to cells in analyzed areas (approximately 2–5 mm from the edge of the well) was estimated at 70,000 $\mu$E using the strain curve described by Gilbert and colleagues(35). The strain parameters were as follows: strain was applied in the form of a square wave with an amplitude of 70,000 $\mu$E with approximately 0.5 second rise time associated with each cycle. Since the observations regarding strained cells were made approximately 2–5 mm from the edge of each well, Applicants presume that the cells portrayed as "strained" in the data contained herein received about 7% stretch. Each strained 6-well Flex I plate was accompanied by a non-strained 6-well Flex II control.

Immunocytochemistry and Microscopy

Immunocytochemical analysis essentially was performed as previously described (34). Briefly, primary human progenitors and preosteoblasts were rinsed with phosphate-buffered saline (PBS), and fixed for 30 minutes at room temperature (RT) with 4% (v/v) paraformaldehyde in PBS. Cells were rinsed twice with PBS, incubated in 50 mM $NH_4Cl$ solution in PBS for 15 minutes to quench the fixative, and then permeabilized with 0.2% Triton X-100 in PBS for 15 minutes at RT. Potential sites for nonspecific antibody binding were blocked by a 30 minute incubation with 2% bovine serum albumin (BSA), 0.2% Triton X-100 and 0.04% sodium azide in PBS at RT. Each immunological co-localization study involved two primary antibodies raised in different species against two distinct antigens. Primary antibodies were typically diluted 1:100 (or used at 1–10 µg/ml) in 2% BSA, 0.2% Triton X-100,), 04% sodium azide in PBS and incubated with the sample for 1 hour at RT. This was followed by four 15 minute washes with 0.02% Triton X-100 in PBS and a 1 hour incubation with an appropriate combination of a secondary indocarbocyanine (Cy3)- and Cy2 cyanine (Cy2)-conjugated goat anti-mouse, goat anti-rabbit or rabbit anti-goat IgG (1:100 dilution in 2% BSA, 0.2% Triton X-100 and 0.04% sodium azide in PBS). The cells were then washed as before with PBS containing 0.2% Triton X-100. The silicone cell culture supports were then excised and mounted on glass microscope slides with Aqua Polymount. The results were analyzed either on Zeiss Fluorescent Microscope (Axioscope) using a 63×oil immersion lens or on a Zeiss laser confocal microscope using a 63×lens. The magnification of the optical system was 630.

Flow Cylometry

Following the enzymatic dissociation, cells were resuspended in serum-free medium and pelleted at 4° C. The pellet was then resuspended in serum-free medium and kept on ice. Equal numbers of strained and of non-strained control cells, ranging from $1-2 \times 10^6$ cells and resuspended in 1 ml of serum-free medium were pipetted into polypropylene test tubes. Cells tested for the cell surface integrin expression were incubated with either 10 µg/ml (anti-$\alpha_v\beta_3$ antibody) or with 1:100 antibody dilution (anti-$\beta_1$ and anti-$\beta_5$ integrin subunit antibodies) or with 1:10 dilution of anti-$\beta_6$integrin subunit antibody for 1 hour on ice. The parallel negative control tubes were incubated with an irrelevant mouse antibody under identical conditions. Following the incubation with a primary antibody, cells were washed extensively in serum-free medium and incubated with the appropriate fluorescein isothiocyanate (FITC)-conjugated secondary goat anti-mouse or goat anti-rabbit IgG at 20 µg/ml for 1 hour on ice. Cells were then washed twice in serum-free medium and finally resuspended in 1 ml of serum-free medium. The fluorescence intensity was analyzed using a Becton Dickinson FACS SCAN flow cytometer.

Western Blot Analysis

Primary human cell cultures were mechanically strained on the Flexcell Strain Apparatus for 48 hours immediately following a replacement of cell culture medium. After the strain, medium was collected and pooled separately from the strained and non-strained wells, and concentrated approximately 6 fold using Omegacell™ 10 ml disposable membrane cells. The protein content in the concentrated medium was determined using a standard Bio-Red method. Medium samples from strained and control cells with equal total protein content were loaded onto a 6% SDS-PAGE gel. Immediately following the electrophoresis, proteins were transferred onto an Immobilon transfer membrane. The efficiency of protein transfer was judged after a 5 minute membrane incubation in Ponceau S solution. Nonspecific antibody binding sites on Immobilon membranes were then blocked by immersing the membrane in a 5% milk and 0.1% Tween 20 in PBS solution overnight at 4° C. Osteopontin was detected by incubating the membranes for 2 hours with anti-osteopontin rabbit polyclonal antibody diluted 1:1000 in 0.1% Tween 20 in PBS at RT, followed by washing the membrane once for 15 minutes and three times for 5 minutes with 0.1% Tween 20 in PBS. Applicants then incubated the membrane with protein A-horseradish peroxidase conjugate diluted 1:2000 in 0.1% Tween 20 in PBS for 1 hour at RT. The final washes included one 15 minute wash and four 5 minute washes in 0.1% Tween 20 in PBS. The antibody binding was detected by exposure to enhanced chemiluminescence using 10 mls of the ECL reagents mix for 60 seconds and then visualized on autoradiography film (Hyperfilm-ECL).

Mineralization Assay

Human bone marrow stromal cells were plated in Flex I and Flex II Type I collagen-coated cell culture dishes at 40,000 cells/well and maintained in α-MEM supplemented with 10% FCS in culture until confluent. Cells were then exposed to osteogenic medium containing α-MEM supplemented with 10% FCS, 10 mM of β-glycerophosphate, 50 mg/ml of ascorbic acid and 40 ng/ml of osteogenic protein OP-1 for 20 days, replacing medium every 3–4 days. For the purposes of this paper, bone marrow stromal cells exposed to these conditions were defined as osteoblasts. Following the incubation in osteogenic medium, cells plated in Flex I dishes were mechanically strained on the Flexcell Strain Apparatus for 48 hours, and then both strained cells and their non-strained controls were examined for the formation of mineralized nodules. Applicants applied a slight modification of the alizarin red-S histochemical staining described previously by Stanford and colleagues(35). Briefly, cells were washed 3 times with PBS and then fixed in 70% ice-cold ethanol for I hour at 4° C. Following 3 water rinses, cells were stained with 0.5% (w/v) alizarin red-S for 10 minutes at room temperature, and then extensively washed with water and PBS.

Alternatively, matrix mineralization was examined via calcein staining. Osteoblasts differentiated in osteogenic medium were washed 3 times with PBS and then fixed in 4% paraformaldehyde for 30 minutes at room temperature. Following 3 PBS rinses and a 30 minute incubation with 2% BSA/PBS, cells were stained with 1 mM calcein in 2% BSA/PBS for 1 hour, and then extensively washed with PBS.

Results

The present studies were carried out using primary human bone marrow stromal cell cultures at distinct functional stages of osteoblast differentiation: progenitors, preosteoblasts and osteoblasts (mineralizing preosteoblasts). The human bone marrow stromal cells cultured under conditions described in Methods, were defined as the osteoprogenitors. In these heterogenous cell cultures, the cells expressing osteopontin, low alkaline phosphatase levels and responding to mechanical strain with an increase in the $\alpha_v\beta_3$ integrin level were considered to be the osteoprogenitors. Preosteoblasts were defined as cells expressing high alkaline phosphatase levels, low or absent osteocalcin and absence of matrix mineralization. Osteoblasts were defined as cells expressing high alkaline phosphatase and osteocalcin levels that were mineralizing their extracellular matrix. These cells were produced by extending the culture of the preosteoblasts.

Figure 1B:
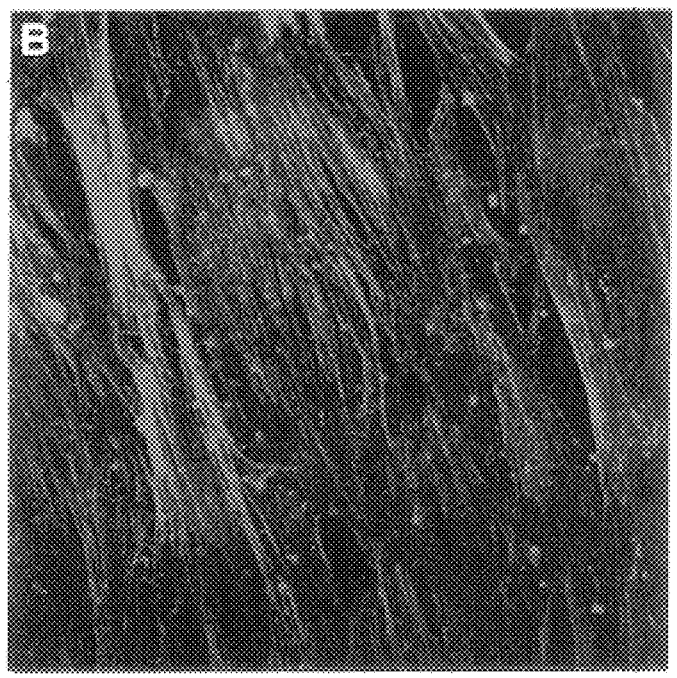
Figure 2A:
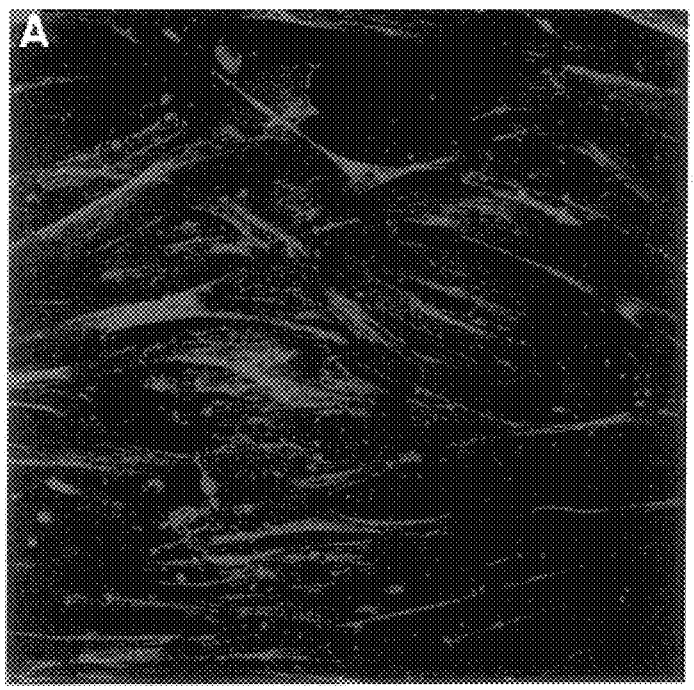
Figure 2B:
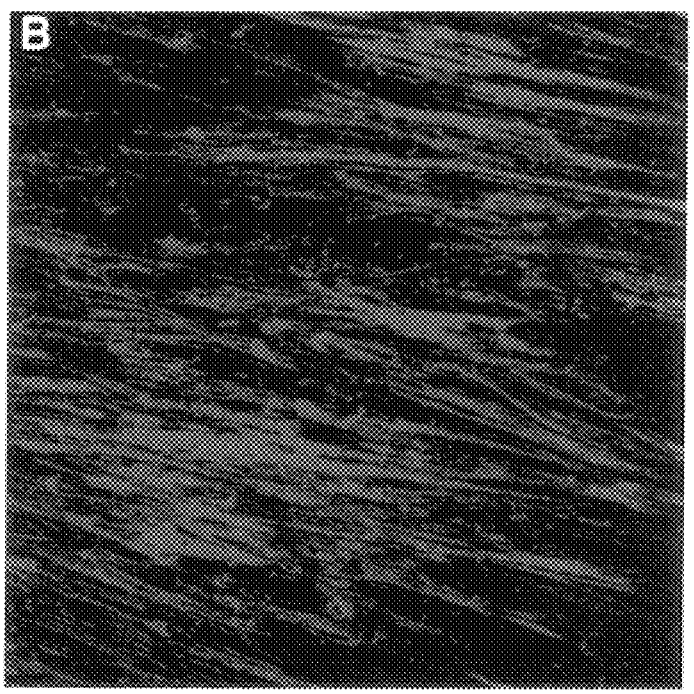
Figure 2C:
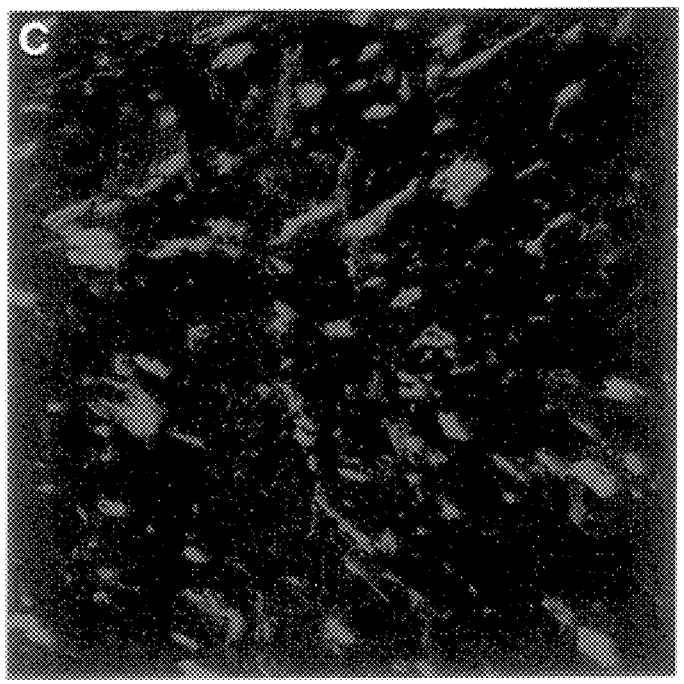
Figure 2D:
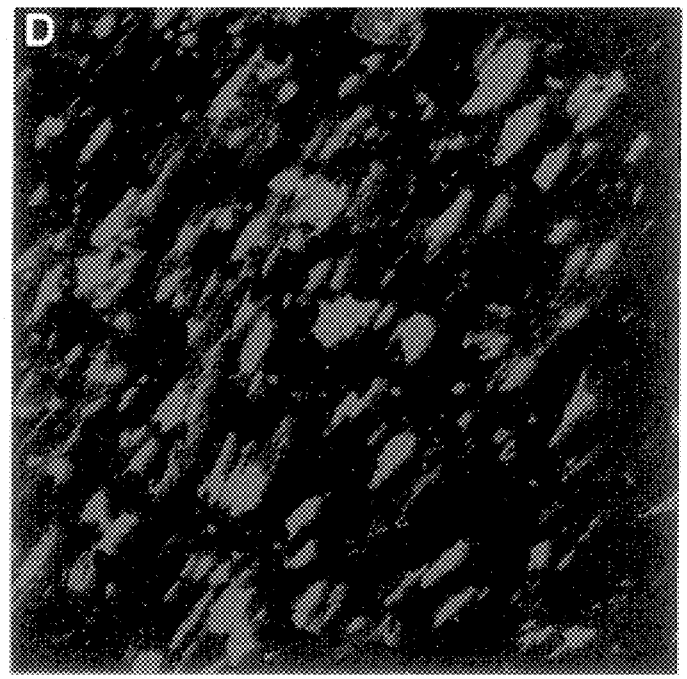

Mechanical Strain Enhances the Expression of the $\alpha_v\beta_3$ Integrin on the Cell Surface of Osteoprogenitors and Preosteoblasts In order to examine whether mechanical strain has a qualitative and/or quantitative effect on the localization and expression level of integrins, near-confluent human preosteoblasts and osteoprogenitors were strained on Flexcell Strain Apparatus, as described in Methods. The applied mechanical strain was the nonuniform strain Applicants have previously described (15) using this apparatus, Using the immunocytochemical approach to immunostain bone cells with an anti-human $\alpha_v\beta_3$ monoclonal antibody, Applicants determined that the cells in human osteoblast lineage utilize $\alpha_v\beta_3$ as a cell surface integrin in our experimental conditions, and that osteoprogenitors (FIGS. 1A and 1B), preosteoblasts (FIGS. 2A and 2B) and osteoblasts (not shown) express the $\alpha_v\beta_3$ integrin. In the presence of Triton X-100, which leads to cell permeabilization and thus, allows examination of the distribution of intracellular as well as cell surface molecules, the uvp, integrin, as detected by an anti-human $\alpha_v\beta_3$ antibody, was localized along actin fibers and in small, granular structures adjacent to actin fibers (FIGS. 1A, 1B, 2A and 2B). Mechanical strain increased the expression of the $\alpha_v\beta_3$ integrin in progenitor cells (FIG. 1B), as compared to non-strained controls (FIG. 1A). Specifically, the number of the $\alpha_v\beta_3$-containing granular structures and the intensity of fluorescence were noticeably increased after 48 hours of cyclic strain. The effect of mechanical strain on the $\alpha_v\beta_3$ integrin expression was particularly well appreciated when cells were stained with tihe anti-$\alpha_v\beta_3$, integrin antibody in the absence of Triton X-100 (FIGS. 1C and 1D). Such a protocol dramatically diminished cell pertneabilization defined by fluorescent 70,000 MW dextran staining (data not shown), and it produced improved focus for the examination of the integrin localization concentrated on the plasma membrane at sites of matrix interaction. Applicants demonstrated that the $\alpha_v\beta_3$, integrin on the cell surface was expressed in large, plaque-like sites of cell-matrix interaction, and it was not expressed in focal adhesions as discussed below. Upon exposure of progenitor and preosteoblast cells to 48 hours of mechanical strain, the number and size of the plaque-like sites increased significantly, and these complexes assumed an organized, directional pattern (FIG. 1D and FIG. 2D). In preosteoblasts, the effect of mechanical strain was in addition to a stimulation by OP-1 of the number of the plaque-like cell/matrix areas of the $\alpha_v\beta_3$ expression (compare FIG. 1C with FIG. 2C).

Figure 3A:
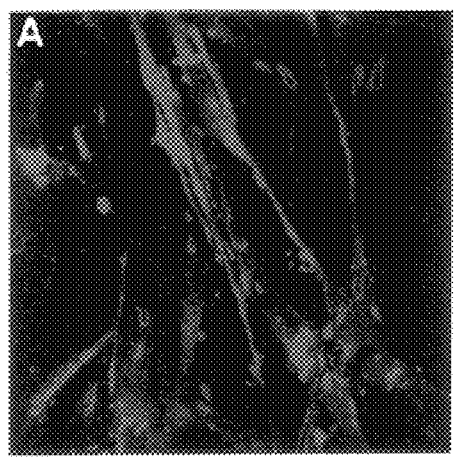
Figure 3B:
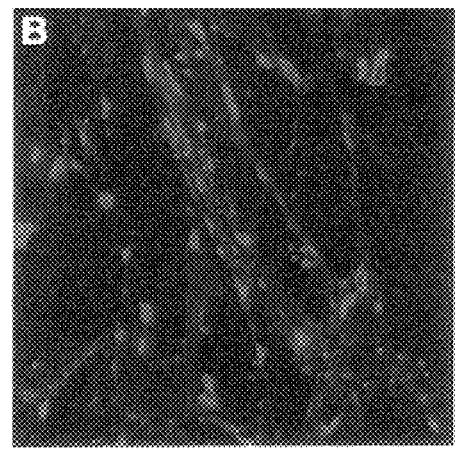
Figure 3C:
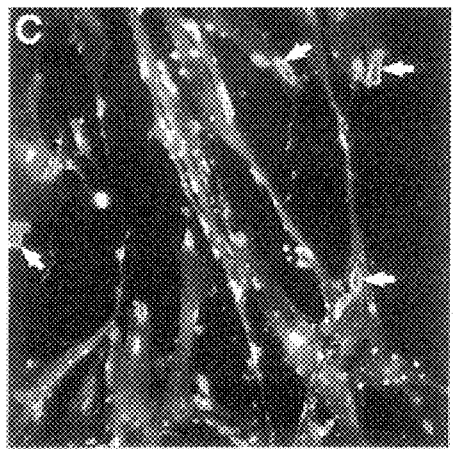

To better characterize the large, plaque-like sites of matrix organization, Applicants examined colocalization of an anti-$\alpha_v\beta_3$ integrin antibody with antibodies directed against Focal Adhesion Kinase (FAK), talin and vinculin in non-perneabilized cells. As shown in FIG. 3, FAK (FIG. 3A) and $\alpha_v\beta_3$ integrin (FIG. 3B) localized to the blotchy plaques on the cell surface of human bonc cells. Each plaque containing the $\alpha_v\beta_3$ integrin also contained FAK (FIG. 3C), but the precise pattern of expression of each protein in a single plaque was different. Microscopic analysis of the cell surface plaques revealed abundant $\alpha_v\beta_3$ integrin present throughout the surface of the plaques (FIG. 3B), whereas the expression of FAK was confined to the boundaries of each blotchy plaque (see arrows in FIG. 3C). Vinculin and talin were not localized to the plaque-like areas of cell surface $\alpha_v\beta_3$ integrin expression (data not shown), but they were found in sites of cell-matrix interaction which were defined as osteoblastic focal adhesion complexes (see FIG. 9A).

Flow Cytometry Confirmned thiat Mechanical Strain Increased the Cell Surface Expression of the $\alpha_v\beta_3$ Integrin in Progenitors, Preosteoblasts, and Osteohiasts The enhancement of the $\alpha_v\beta_3$ integrin expression on the cell surface of ostcoprogenitors, preosteoblasts and osteoblasts, as detected by immunocytochemical techniques, was confirmed by flow cytometric analysis. FIG. 4 shows two representative plots of flow cytometric analysis of the $\alpha_v\beta_3$ integrin expression. In the right panel, Applicants demonstrated a shift in the fluorescence from non-strained (B') to mechanically strained preosteob lasts (D') shown in the overlay panel, which indicates an increase in the preosteoblast cell surface expression of the $\alpha_v\beta_3$ with strain. As shown in the left panel of FIG. 4, a similar shift in fluorescence was detected after osteoprogenitors were mechanically strained, hence showing that strain also increased the cell surface expression of the $\alpha_v\beta_3$ in these cells and thus corroborating our immunocytochemical results.

As demonstrated by flow cytometry in three to five experiments/cell type using, an anti-human $\alpha_v\beta_3$ integrin antibody to react with single cell suspensions of osteob last lineage cells, the mean fluorescence of the integrin on the cell surface of osteoprogenitors was increased significantly from 49.3±2.7 in non-strained cells to 78.3±6.7 in mechanically strained cells (Table 1). Similarly, in preosteoblasts, Applicants detected a remarkable mean fluorescence chance from 45.3±8.5 in control cells to 90.0±6.6 in strained cells. Further differentiation of preosteoblasts in OP-1-containing osteogenic medium to cells expressing osteocalcin and mineralizing the extracellular matrix (osteoblasts) lead to an increased fluorescence intensity due to increased $\alpha_v\beta_3$ integrin expression in strained cells (59.8±10.6) as compared to non-strained cells (43.2±7.0).

TABLE 1

| CELL TYPE | | MEAN FLUORESCENCE ± SE |
| --- | --- | --- |
| Progenitors | Not strained | 49.3 ± 2.7 |
| | Strained | 78.3 ± 6.7* |
| Preosteoblasts | Not strained | 45.3 ± 8.5 |
| | Strained | 90.0 ± 6.6* |
| Mineralizing | Not strained | 43.16 ± 7.0 |
| Preosteoblasts | Strained | 59.8 ± 10.6* |

Table 1. Changes in mean fluorescence as a measure of the $\alpha_v\beta_3$ integrin stimulation by mechanical strain. The flow cytometric analysis was performed in single cell suspensions of cells mechanically strained for 48 hours as well as in their non-strained controls. Osteoprogenitors, preosteoblasts and mineralizing preosteoblasts were incubated with a mouse monoclonal antibody directed against anti-human $\alpha_v\beta_3$ integrin, followed by an incubation with a secondary FITC-conjugated anti-mouse antibody, as described in Methods. Each data point is a mean of at least 3 experiments. *, $p \leq 0.01$ compared to cells not strained.

TABLE 2

| $\alpha_v$ integrin type | Blotchy cell-matrix interactions | Focal adhesions | Cell projections | Expressions in cytosol |
|---|---|---|---|---|
| $\alpha_v\beta_1$ | − | + | − | + |
| $\alpha_v\beta_3$ | + | − | + | + |
| $\alpha_v\beta_5$ | − | − | + | + |
| $\alpha_v\beta_6$ | − | − | − | + |

Table 2. Summary of specific integrin localization sites in bone cells. In addition to their expression in the cytosol, the $\alpha_v\beta_1$ integrin is apparently present in focal adhesions, the $\alpha_v\beta_3$ integrin is evident in blotchy cell-matrix interactions, and the $\alpha_v\beta_5$ integrin is found in cellular projections.

Mechanical Strain Increases Osteopontin Secretion into Osteoprogenitor Medium

Figure 5A:
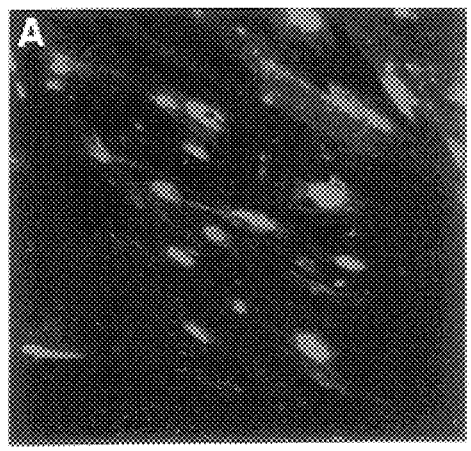
Figure 5B:
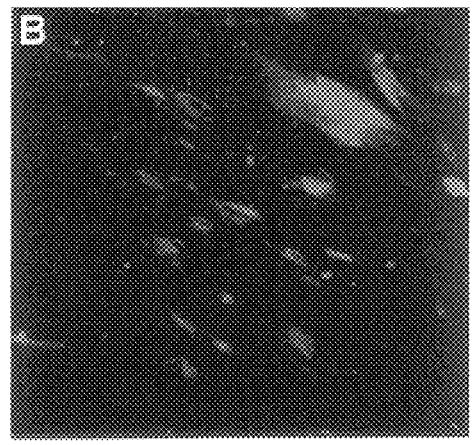

Using immunocytochemical techniques, Applicants demonstrated that human bone cells express osteopontin, a ligand for the $\alpha_v\beta_3$ integrin (FIG. 5A). In addition, Applicants observed a high degree of colocalization (FIG. 5C) between osteopontin (FIG. 5A) and the $\alpha_v\beta_3$ integrin (FIG. 5B) in non-permeabilized bone cells. Osteopontin co-localized with the $\alpha_v\beta_3$ integrin in the large plaque-like areas of cell matrix interaction. This finding coupled with the elevated level of $\alpha_v\beta_3$ integrin found in mechanically loaded cells suggests that in response to mechanical strain, osteopontin may serve as an integrin ligand.

Applicants also addressed the issue whether osteopontin levels, both intracellular and secreted into cell culture media, were affected by mechanical strain. By performing Western blot analyses using anti-human osteopontin antibodies, Applicants detected several forms of osteopontin that were secreted into bone cell culture medium (FIG. 6A). The predominant osteopontin band had a molecular size of approximately 168 kDa and may represent either a cross-linked osteopontin-matrix protein macro-molecule or an osteopontin homomultimer (FIG. 6A). In cell lysates, the osteopontin bands included predominant 75 kDa and a 78 kDa bands (FIG. 6B). The 75 kDa band has been frequently seen in several cell types as a mature OPN(36,37). FIG. 6A is representative of five experiments demonstrating stimulation of osteopontin secretion into the medium of mechanically strained cells in the osteoblast differentiation program. The strain over control stimulation index determined by scanning densitometry of the 168 kDa bands was more than 2.0 in osteoprogenitors and approximately 1.0 for preosteoblasts. The level of osteopontin secretion in non-strained osteoprogenitors in the presented blots seems lower than that in non-strained preosteoblasts exclusively due to technical reasons (as not to overexpose the band representing strained progenitors). Thus, the effect of strain was apparent only in the osteoprogenitors. In contrast to the findings in cell culture mediums, Western blotting of cell lysates revealed predominant osteopontin bands of 75 and 78 kDa and no differences in osteopontin levels between strained and non-strained bone cells, regardless of the cell differentiation stage (FIG. 6B). These data suggest that the effect of strain includes stimulation of secretion of the 168 kDa molecule such that it does not accumulate in the cell.

$\alpha_v\beta_3$ Integrin Colocalizes with Tissue Transglutaminase

Figure 7A:
Figure 7B:
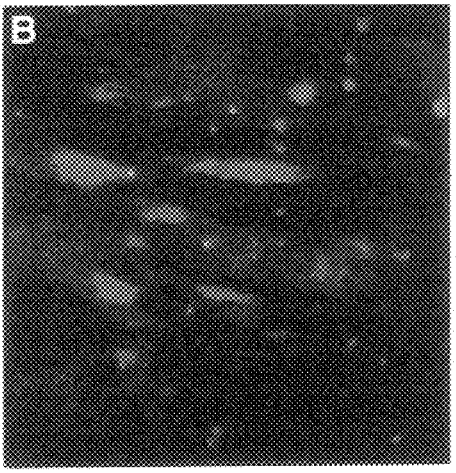
Figure 7C:
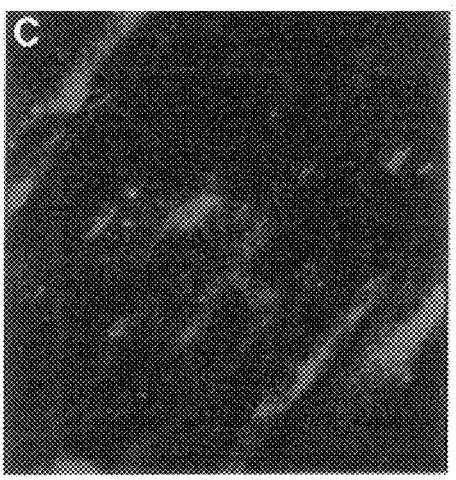
Figure 7D:
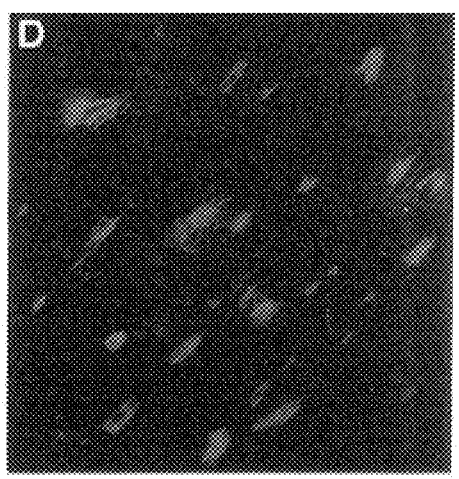
Figure 7E:
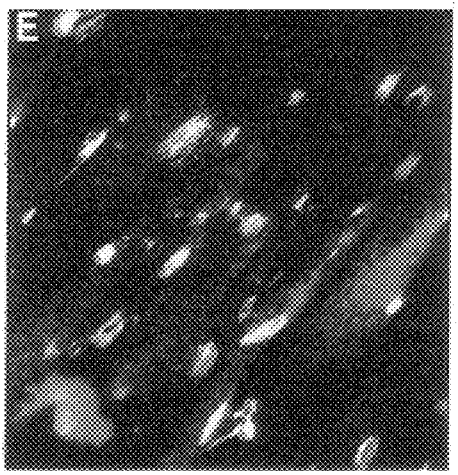
Figure 8A:
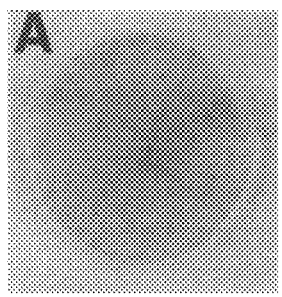
Figure 8B:
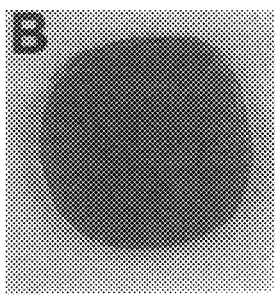
Figure 8C:
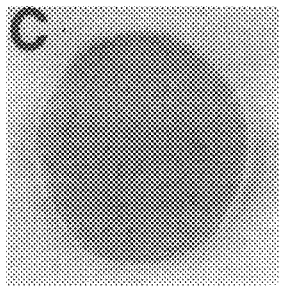
Figure 8D:
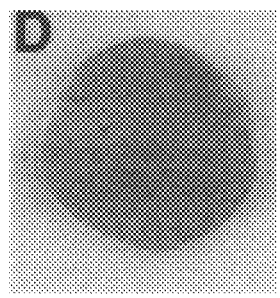
Figure 8E:
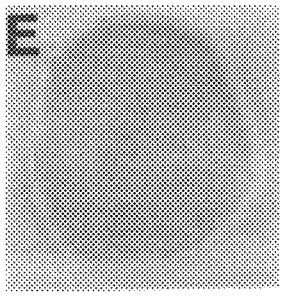
Figure 8F:
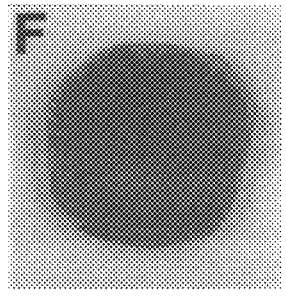
Figure 8G:
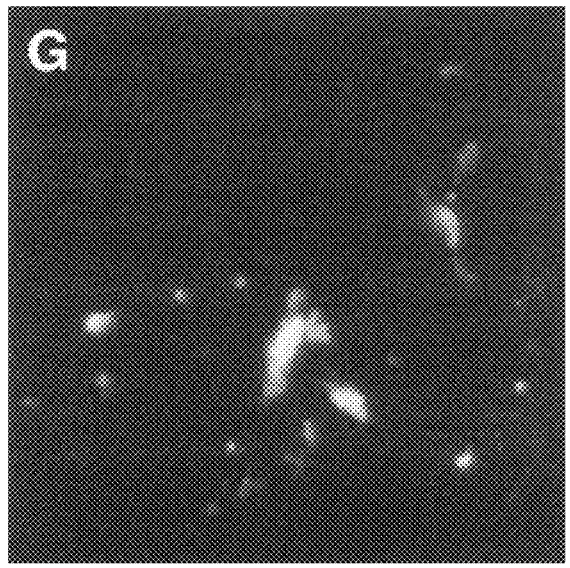

To further analyze the basis of the large osteopontin molecular sizes, Applicants analyzed whether mechanical strain affected osteoblastic expression of tissue transglutaminase, which cross-links proteins into homo and heteromultimers through the formation of $\gamma$-glutamyl-$\Sigma$-lysine cross-links between substrate proteins. Bone osteopontin and osteonectin are tissue transglutaminase substrates(38–40). Based on the immunocytochemical analysis, tissue transglutaminase in osteoprogenitors is expressed throughout the cytoplasm in punctate subcellular structures, as shown in detergent-permeabilized cells (FIG. 7A). Interestingly, in cells fixed in the absence of Triton X-100, tissue transglutaminase was also found in large, plaque-like sites (FIG. 7B and FIG. 7C) that closely resemble the cell surface $\alpha_v\beta_3$ integrin plaques (FIG. 7D). Moreover, the immunocytochemical approach demonstrated a colocalization of tissue transglutaminase and $\alpha_v\beta_3$ integrin in well defined plaques in osteoprogenitors (FIG. 7E).

The Effect of Mechanical Strain on Formation of Mineralized Nodules

Since osteoblasts are known to produce, deposit and mineralize the bone matrix, Applicants examined the influence of mechanical strain on the formation of mineralized nodules. Alizarin red S histochemical staining of osteoblasts derived from bone marrow stromal cells demonstrated that although mineralization was detected in both strained (FIGS. 8B, 8D, 8F) and non-strained cultures (FIGS. 8A, 8C, 8E), the intensity of nodules produced by mechanically strained cells was dramatically enhanced at least twofold, as compared with controls. These osteoblastic cells were maintained in osteogenic medium containing ascorbate, $\beta$-glycerophosphate and OP-1 for 18 days prior to 48 hours of mechanical strain (days 18–20). Furthermore, on the basis of colocalization of another mineralization marker, calcein with the anti-$\alpha_v\beta_3$ integrin antibody (FIG. 8G) in osteoblasts derived from bone marrow stromal cells, Applicants observed that the $\alpha_v\beta_3$ integrin plaques colocalized with calcein-labeled mineralization nodules. Moreover, in mineralizing cultures the $\alpha_v\beta_3$ plaques assumed a nodular shape (FIG. 8G) indicated by their expansion in the Z axis (vertically), unlike their level, flatter shape observed in non-mineralizing cells (compare with FIG. 1D and FIG. 2D).

Mechanical Strain does not Affect Osteoblastic Focal Adhesions

Figure 5C:
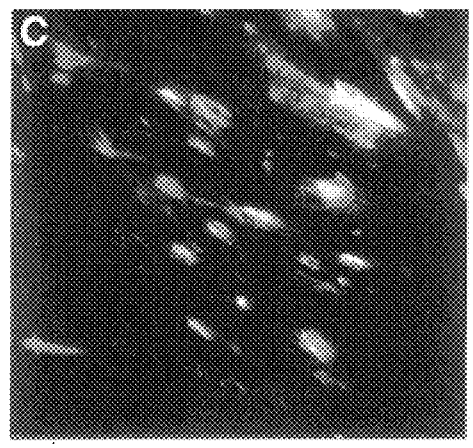
Figure 9A:
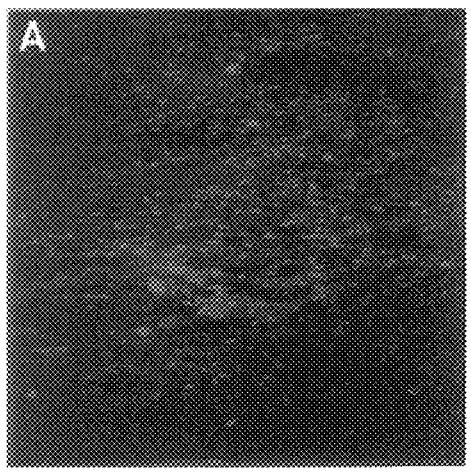

Application of a monoclonal anti-human $\alpha_v$ antibody in our immunocolocalization protocol followed by confocal analysis demonstrated that the $\alpha_v$ subunit epitope detected by monoclonal antibody L230 was present in the plaque-like areas of cell-matrix interaction discussed above, but it was predominantly found in fine, regularly and densely spaced structures morphologically similar to focal adhesions described in other cell types (41–43). These focal adhesions were observed in each of the osteoblast differentiation stages examined (FIG. 9A). Besides their characteristic shape, the structures containing the $\alpha_v$ subunit were defined as focal adhesions on the basis of their co-localization with known focal adhesion markers vinculin and talin. Interestingly, an identical pattern of $\alpha_v$ localization was obtained in both permeabilized and non-permeabilized cells, thus suggesting that this $\alpha_v$ subunit epitope is primarily exposed during cell surface/substratum interaction. Moreover, our results indicate a high level of focal adhesion expression in resting osteoblastic cell cultures obscuring the effects of mechanical strain on the level of $\alpha_v$ integrin expression in the focal adhesion of human bone cells. Studies showing a cell surface colocalization of the $\alpha_v$ subunit (L230 antibody) with osteopontin in plaque-like structures provided proof that this $\alpha_v$ subunit was also found in the $\alpha_v\beta_3$ integrin plaques, since osteopontin colocalized closely with the $\alpha_v\beta_3$ in those plaques (FIG. 5C).

Figure 9B:
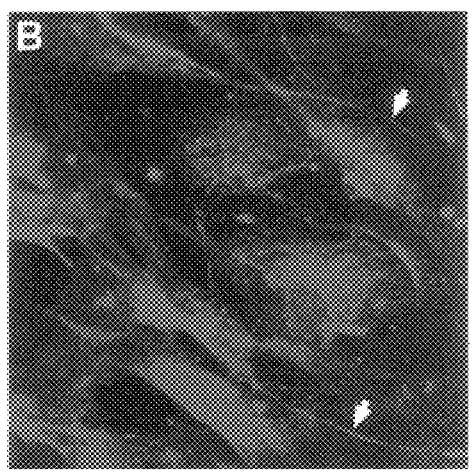
Figure 9C:
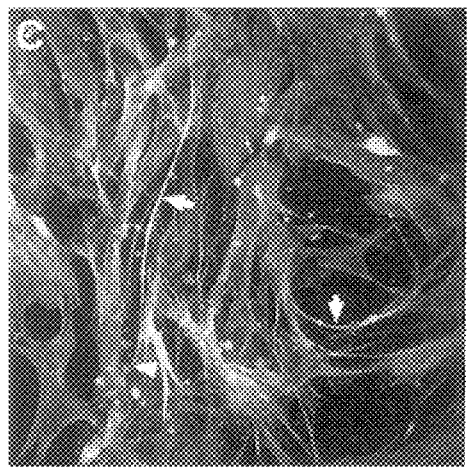
Figure 9D:
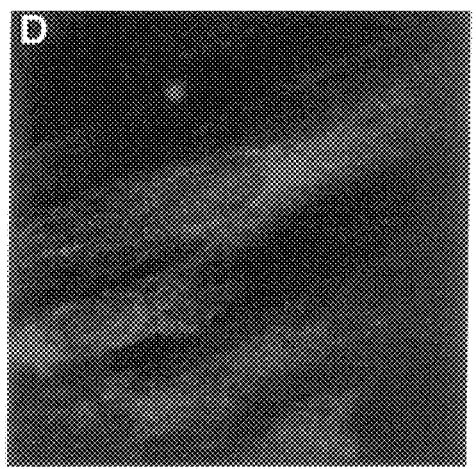

To identity the $\beta$ subunit of the $\alpha_v\beta$ heterodimer detected in the focal adhesions of our bone cell cultures (FIG. 9A), Applicants immunologically colocalized the anti-$\alpha_v$ antibody with each of the potential $\alpha_v\beta$ candidate heterodimers of the osteoblast. The anti-$\beta_5$ and the anti-$\beta_6$ integrin subunit antibodies revealed a cytoplasmic distribution of these integrins distinct from the $\alpha_v$ subunit—containing fine focal adhesions, as shown in FIGS. 9B and 9D, respectively. Interestingly, the colocalization of the $\beta_5$ integrin subunit and the $\alpha_v\beta_3$ integrin revealed that our human bone cell cultures were characterized by long cellular projections containing both the $\alpha_5$ subunit and the $\alpha_v\beta_3$ integrin (FIG. 9B and FIG. 9C). These cellular projections abut other cell bodies at their end, thus, suggesting the involvement of the $\alpha_v\beta_5$ integrin in cell-cell communication (see arrows in FIG. 9C). As demonstrated by flow cytometry, mechanical strain increases the expression of the $\alpha_5$ integrin subunit by approximately 25% on the surface of preosteoblasts, but not on the osteoprogenitor plasma membrane.

In contrast to the $\beta_5$ subunit, the $\beta_6$ integrin subunit expression level, as measured by flow cytometry, was not affected at all by mechanical strain. The immunolocalization studies demonstrated that the primarily cytosolic staining pattern of the $\beta_6$ integrin subunit was different from that of fine focal adhesions containing the $\alpha_v$ subunit (FIG. 9D). This is the first demonstration of the $\alpha_v\beta_6$ integrin in osteoblasts.

Figure 10B:
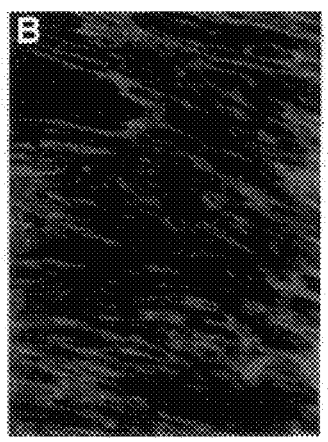
Figure 10C:
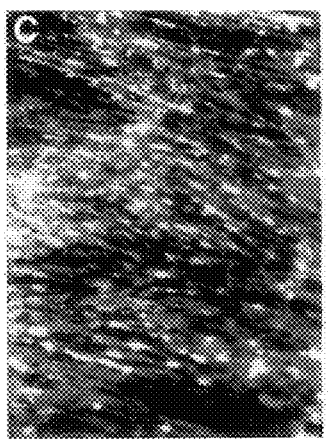

Finally, Applicants compared the distribution of the $\beta_1$ integrin subunit with the staining pattern of fine focal adhesions (FIG. 10). As shown in FIG. 10B, the $\beta_1$ integrin subunit was expressed in a rather diffuse staining pattern, as expected from the large number of osteoblastic $b_1$ integrins. However, the immunochemical analysis indicated that a significant portion of the $\beta_1$ integrin subunit colocalized closely with the $\alpha_v$ integrin subunit, as shown in FIG. 10C. Careful microscopic analysis of a large number of samples demonstrated that the $\alpha_v$ and $\beta_1$ integrin subunits are present in the focal adhesions of osteoprogenitors, preosteoblasts and osteoblasts.

Discussion

Applicants have demonstrated strain-induced osteoblastic mineralization in vitro. It provides several important new clues as to the molecular basis of the cellular events that lead to mechanical strain induced bone formation. The general conclusion from this investigation is that in response to mechanical strain, the $\alpha_v\beta_3$ integrin of the osteoblast lineage is upregulated and that it may participate in the organization of the osteopontin-containing extracellular matrix in unique plaque-like areas of cell-matrix interaction.

Applicants have presented evidence that primary human cells of the osteoblast lineage express at least two types of cell-matrix interactions. One type represents fine and densely spaced cell surface structures that colocalize with vinculin and represent osteoblastic focal adhesions. A second type of relatively large, plaque-like areas of integrin/extracellular matrix protein interaction colocalizes with Focal Adhesion Kinase (FAK) but not with vinculin. Applicants have demonstrated that the $\alpha_v\beta_3$ integrin specifically colocalizes to the second type of cell-matrix interaction sites and that its expression was further stimulated by mechanical strain. Upon mechanical strain, both types of cell-matrix interactions assumed an organized, directional pattern (FIG. 1D and FIG. 9A). In agreement with earlier reports by Buckley and colleagues (49), this new orientation was perpendicular to the vectors of strain. FAK has been previously shown to colocalize with several components of cellular focal adhesions, such as tensin, vinculin and talin (45). Furthermore, these plaque-like areas are specific to the osteoblast lineage in that Applicants have failed to demonstrate them in other cell types (i.e. human melanoma cells), and cells differentiating from hematopoetic progenitors (i.e. macrophages and osteoclasts).

Applicants also demonstrated that the $\alpha_v\beta_5$ integrin once considered a dominant osteoblast adhesion molecule is largely cytoplasmic in primary human bone cells, and that it is also expressed along extended cellular projections that contact distant osteoblast cell bodies. Applicants believe that these cellular projections participate in cell—cell communication.

Applicants have also identified at least one matrix protein, osteopontin as a ligand for the $\alpha_v\beta_3$ integrin contained in the plaque-like cell-matrix organization sites. Osteopontin in our studies in the osteoblast may act as an autocrine matrix protein, secreted in the focal adhesion in response to regulatory stimuli and important in the proliferation and differentiation of cells during the osteoblast program. Based on previous reports, osteopontin is present in human milk and melanoma cells, as well as in rat osteosarcoma cells as an approximately 75 kDa protein, and in osteoclasts as a protein of 55–65 kDa (36,37,47–48). Applicants have demonstrated the presence of several osteopontin bands of different molecular sizes in the cell culture medium of osteoprogenitors and osteoblasts. The osteopontin band of highest intensity was detected at approximately 168 kDa, thus representing a cross-linked macromolecular complex of either osteopontin and other matrix proteins or of osteopontin oligomers.

Applicants have discovered that in human cells of the osteoblast lineage, osteopontin colocalizes with the $\alpha_v\beta_3$ integrin in plaque-like sites of cell-matrix interaction. Moreover, the $\alpha_v\beta_3$ integrin was found in the mineralization nodules in osteoblasts derived from bone marrow stromal cells, as determined by anti-$\alpha_v\beta_3$ antibody/calcein staining. Applicants also demonstrated that mechanical strain leads to an increased formation of mineralized nodules (FIG. 9). Osteopontin and other extracellular proteins (including fibronectin and bone sialoprotein) were previously shown to initiate and/or direct the spatial deposition of mineral in the extracellular matrix (49–51). Therefore, Applicants' results indicate that mechanical strain-enhanced interaction between osteopontin and $\alpha_v\beta_3$ integrin is indicated to lead to enhanced matrix mineralization.

Osteopontin, a known substrate of tissue transglutaminase, may be covalently cross-linked by this enzyme (52). Tissue transglutaminases are a widely distributed class of enzymes found intra- as well as extracellularly (53). Tissue transglutaminase participates in the assembly and organization of extracellular matrix via its activity as an externalized enzyme, and thus has an impact on cell spreading and adhesion (54). Tissue transglutaminase catalyzes a calcium-dependent formation of a specific isopeptide bond, therefore promoting intra- and/or intermolecular cross-linking in proteins (55). Tissue transglutaminase is a highly selective enzyme, with only a few native proteins identified as its substrates (53,56). The high specificity of this enzyme renders the tissue transglutaminase-catalyzed cross-linking of proteins, including osteopontin, physiologically significant.

Our study indicates that the $\alpha_v\beta_3$ integrin colocalizes with tissue transglutaminase in bone cells (FIG. 7), and suggests that osteopontin colocalizes with tissue transglutaminase in the large, blotchy sites of matrix organization, thus suggesting that other matrix proteins may be cross-linked with osteopontin in these complexes.

Finally, Burger and Veldhujzen have reported that production of extracellular matrix decreases at high strain levels, while cellular proliferation increases (57). Applicants observed the enhancement of mineralization of extracellular matrix in osteoblasts grown in osteogenic medium for 20 days, resulting from an average mechanical strain level of approximately 70,000 $\mu E$, as determined on the basis of the strain curve described by Gilbert et al (33). Thus, Applicants suggest that the majority of the cells in our studies were exposed to a strain level at which no inhibition of bone matrix production occurred. Since Applicants were limited to a non-uniform strain distribution by our apparatus, Applicants were unable to determine the applied strain that lead to increased mineralization. Our data indicates that the sequential process of matrix production, deposition and mineralization was enhanced by the level of mechanical strain employed.

In view of the above, it will be seen that the several objects of the invention are achieved.

As various changes could be made in the above compositions and processes without departing from the scope of the invention, it is intended that all matter contained in the above description be interpreted as illustrative and not in a limiting sense.

REFERENCES

1. Wozney, J. J., Rosen, V., Celeste, A. J., Mitsock, L. M., Whiters, M. J., Kriz, R. W., Hewick, R. M., and Wang, E. A. (1988) *Science* 242, 1528–1534
2. Cheng, S.-L., Yang, J. W., Rifas, L., Zhang, S. -F., and Avioli, L. V. (1994) *Endocrinology* 134, 277–286
3. Lecanda, F., Avioli, L. V., and Cheng, S. L. (1997) *J. Cell. Biochem.* (In press)
4. Hanada, K., Dennis, J. E., and Caplan, A. I. (1997) *J. Bone Miner. Res.* 12, 1606–1614
5. Owen, M. (1988) *J. Cell Sci. Suppl.* 10, 63–76
6. Caplan, A. I. (1991) *J. Orthop. Res.* 9, 641–650
7. Yamaguchi, A., Katagiri, T., Ikeda, T., Wozney, J. M., Rosen, V., Wang, E. A., Kahn, A. J., Suda, T., Yoshiki, S. (1991) *J. Cell Biol.* 113, 681–687
8. Katagiri, T., Yamaguchi, A., Komaki, M., Abe, E., Takahashi, N., Ikeda, T., Rosen, V., Wozney, J. M., Fujisawa-Sehara, A., and Suda, T. (1994) *J. Cell. Biol.* 127, 1755–1766
9. Katagiri, T., Yamaguchi, A., Ikeda, T., Yoshiki, S., Wozeny, J. M., Rosen, V., Wang, E. A., Tanaka, H., Omura, S., and Suda, T. (1990) *Biochem. Biophys. Res. Comm.* 172, 295–299
10. Aubin, J. E. and Kahn, A. (1996) in *Primer on the metabolic bone diseases and disorders of mineral metabolism* (Favus, M. J., ed) pp. 35–38, Lippincott-Raven, Philadelphia, New York
11. Pead, M. J., Skerry, T. M., and Lanyon, L. E. (1988) *J. Bone Miner. Res.* 3, 647–656
12. Brighton, C. T., Fisher, J. R. S., Levine, S. E., Corsetti, J. R., Reilly, T., Landsman, A. S., Williams, J. L., and Thibault, L. E. (1996) *J. Bone and Joint Surg.* 78, 1337–1347
13. Einhom, T. A. (1998) *J. Bone Miner. Res.* 13, 10–12
14. Ingber, D. E. (1997) *Ann. Rev. Physiol.* 59, 575–599
15. Harter, L. V., Hruska, K. A., and Duncan, R. L. (1995) *Endocrinology* 136, 528–535
16. Toma, C. D., Ashkar, S., Gray, M. L., Schaffer, J. L., and Gerstenfeld, L. C. (1997) *J. Bone Miner. Res.* 12, 1626–1636
17. Salter, D. M., Robb, J. E., and Wright, M. O. (1997) *J. Bone Miner. REs.* 12, 1133–1141
18. LaFlamme, S. E. and Auer, K. L. (1996) *Cancer Biology* 7, 111–118
19. Schwartz, M. A., Schaller, M. D., and Ginsberg, M. H. (1995) *Annu. Rev. Cell Biol.* 11, 549–600
20. Sanchez-Mateos, P., Cabanas, C., and Sanchez-Madrit, F. (1996) *Seminars in Cancer Biology* 7, 99–109
21. Sonnenberg, A. (1993) *Current topics in microbiology and imnmunology* 184, 7–35
22. Craig, S. W. and Johnson, R. P. (1996) *Curr. Opin. Cell. Biol.* 8, 74–85
23. Denhardt, D. T. and Guo, X. (1993) *FASEB J.* 7, 1475–1482
24. Grzesik, W. J. and Robey, P. G. (1994) *J. Bone Miner. Res.* 9, 487–496
25. Miyauchi, A., Alvarez, J., Greenfield, R. M., Teti, A., Grano, M., Colucci, S., Zambonin-Zallone, A., Ross, F. P., Teitelbaum, S. L., Cheresh, D., and Hruska, K. A. (1991) *J. Biol. Chem.* 266, 20369–20374
26. Oldberg, a. Franzen, A., Heinegard, D., Pierschbacher, M., and Ruoslahti, E., (1988) *J. Biol. Chem.* 263, 19433–19436
27. Sauk, J. J., Van Kampen, C. L., Foster, N. K., and Somerman, M. J. (1990) *Experimental Cell Research* 188, 105–110
28. Sommernan, J. J., Prince, C. P., Sauk, J. J., Foster, R. A., and Moehring, J. M. (1989) *Matrix* 9, 49–54
29. Sommerman, J. J., Prince, C. W., Sauk, J. J., Foster, R. A., and Butler, W. T. (1987) *J. Bone Miner. Res.* 2, 259–265
30. Ross, F. P., Chappel, J., Alvarez, J. I., Sander, D., Butler, W. T., Farach-Carson, M. C., Mintz, K. A., Robey, P. G., Teitelbaum, S. L., and Cheresh, D. A. (1993) *J. Biol. Chem.* 268, 9901–9907
31. Cheresh, D. A. and Spiro, R. C. (1987) *J. Biol. Chem.* 262, 17703–17711
32. Smpath, T. K., Maliakal, J. C., Hauschka, P. V., Jones, W. K., Sasak, H., Tucker, R. F., White, K. H., Coughlin, J. E., Tucker, M. M., Pag, R. H. L., Corbett, C., Ozkaynak, E., Oppermann, H., and Rueger, D. C. (1992) *J. Biol. Chem.* 267, 20352–20362
33. Gilbert, J. A., Weiinhold, P. S., Banes, A. J., Link, G. W., and Jones, G. L. (1994) *J. Biomechnaics* 27, 1169–1177
34. Wozniak, M. and Limbird, L. E. (1996) *J. Biol. Chem.* 271, 5017–5024
35. Stanford, C. M., Jacobson, P. A., Eanes, E. D., Lembke, L. A., and Midura, R. J. (1995) *J. Biol. Chem.* 270, 9420–9428
36. Kubota, T. M., Yamauchi, M., Onozaki, S. S., Suzuki, Y., and Sodek, J. (1993) *Archives of Oral Biology* 38, 23–30
37. Senger, D. R., Peruzzi, C. A., Papadopoulos, A., and Tenen, D. G. (1989) *Biochimica et Biophysica Acta* 996, 43–48
38. Prince, C. W., Dickie, D., and Krumdieck, C. L. (1991) *Biochemical and Biophysical Research Communications* 177, 1205–1210
39. Aeschlimann, D., Wetterwald, A., Fleisch, H., and Paulsson, M. (1993) *J. Cell Biol.* 120, 1461–1470
40. Sorensen, E. S., Rasmussen, L. K., Moller, L., Jensen, P. H., Hojrup, P., and Petersen, T. E. (1994) *Biochemistry Journal* 304, 13–16
41. Hotchin, N. A. and Hall, A. (1995) *J. Cell Biol.* 131, 1857–1865
42. Laijava, H., Pletonen, J., Akiyama, S. K., Yamada, S. S., Gralnick, H. R., Uitto, J., and Yamada, K. M. (1990) *J. Cell. Biol.* 110, 803–815
43. Ridley, A. J. and Hall, A. (1992) *Cell* 70, 389–399
44. Buckley, M. J., Banes, A. J., and Jordan, R. D. (1990) *J. Oral Maxillofac Surg* 48, 276–45. Zachary, I. And Rozengurt, E. (1992) *Cell* 71, 891–894

46. Hruska, K. A., Rolnick, F., Huskey, M., Alvarez, U., and Cheresh, D. (1995) *Endocrinology* 136, 2984–2992
47. Chellaiah, M. and Hruska, K. A. (1996) *Mol. Biol. Cell* 7, 743–753
48. Chellaiah, M., Fitzgerald, C., Filardo, E. J., Cheresh, D. A., and Hruska, K. A. (1996) *Endocrinology* 137, 2432–2440
49. Chen, Y., Bal, B. S., and Gorski, J. P. (1992) *J. Biol. Chem.* 267, 24871–24878
50. Gerstenfeld, L. C., Gotoh, Y., McKee, M. D., Nanci, A., Landis, W. J., and Glimcher, M. J. (1990) *Anat Rec* 228, 93–103
51. Hunter, G. K. and Goldberg, H. A. (1993) *PNAS* 90, 8562–8565
52. Beninati, S., Senger, D. R., Cordella-Miele, E., Mukhedjee, A. B., Chcckalaparampil, I., Shanmugam, V., Singh, K., and Mukherjee, B. B. (1994) *Journal of Biochemistry* 115, 675–682
53. Aeshlimann, D. and Paulsson, M. (1994) *Thrombosis and hiemostasis* 71, 402–415
54. Jones, R. A., Nicholas, B., Mian, S., Davies, P. J. A., and Griffin, M. (1997) *Journal of Cell Science* 110, 2461–2472
55. Folk, J. E. (1980) *Ann. Rev. Biochiem.* 49, 517–531
56. Aeschlimann, D., Kaupp, O., and Paulsson, M. (1995) *J. Cell Biol.* 129, 881–892
57. Burger, E. H. and Veldhuijzen, J. P. (1993) in *Bone—Bone Growth* (Hall, K., ed) pp. 37–56, CRC Press, Melbourne

What is claimed is:

1. A method of measuring new bone formation comprising extracting bone marrow stromal cells from bone marrow cavities and growing said cells to subconfluence, exposing said cells to a candidate medium or regimen for osteogenesis or inhibition of osteogenesis, and determining the development of alpha sub v beta sub 3 integrin-containing plaque.

2. The method of claims 1 further comprising the steps of comparing the development of said plaque generated using said candidate medium or regimen with the development of said plaque using a control.

3. The method of claim 2 wherein said control is a bone morphogenetic factor.

4. The method of claim 3 wherein said bone morphogenetic factor is bone morphogenetic protein-7 (BMP-7).

5. The method of claime 1 wherein said plaque sites further contain focal adhesion kinase.

6. The method of claim 1 wherein said examination further comprises measurement of the number and size of said plaque sites.

7. The method of claim 1 further comprising microscopically photographing said plaque sites and digitizing components thereof for precision measurements.

8. The method of claim 1 wherein said examination further comprises utilization of flow cytometry.

9. A method for screening the bone formation capacity of sample cells comprising exposing said cells to a medium or regimen known to generate osteogenesis, and determining the development of alpha sub v beta sub 3 integrin-containing plaque.

10. The method of claim 9 wherein the medium or regimen comprises a bone morphogenetic factor.

11. The method of claim 10 wherein the factor comprises bone morphogenetic protein-7 (BMP-7).

12. The method of claim 9 a wherein said plaque sites further contain focal adhesion kinase.

13. The method of claim 9 wherein said examination further oonprises measurement of the number and size of said plaque sites.

14. The method of claim 9 further comprising microscopically photographing said plaque sites and digitizing components thereof for precision measurements.

15. The method of claim 9 wherein said examination further comprises utilization of flow cytometry.

16. The method of claim 1 wherein the regimen for osteogenesis comprises exposing the cells to mechanical strain.

17. The method of claim 9 wherein the regimen known to generate osteogenesis comprises exposing the cells to mechanical strain.

* * * * *